US008822543B2

(12) United States Patent
Bassaganya-Riera

(10) Patent No.: US 8,822,543 B2
(45) Date of Patent: Sep. 2, 2014

(54) METHOD OF USING PUNICIC ACID TO ENHANCE IMMUNE RESPONSE AND PREVENT METABOLIC DISORDERS

(75) Inventor: Josep Bassaganya-Riera, Blacksburg, VA (US)

(73) Assignee: Nutrition Therapeutics, Inc., Blacksburg, VA (US)

( * ) Notice: Subject to any disclaimer, the term of this patent is extended or adjusted under 35 U.S.C. 154(b) by 0 days.

(21) Appl. No.: 13/370,378

(22) Filed: Feb. 10, 2012

(65) Prior Publication Data

US 2012/0141542 A1   Jun. 7, 2012

Related U.S. Application Data

(60) Continuation of application No. 12/710,906, filed on Feb. 23, 2010, which is a division of application No. 11/039,419, filed on Jan. 20, 2005, now abandoned, which is a continuation-in-part of application No. 11/031,591, filed on Jan. 7, 2005, now abandoned.

(60) Provisional application No. 60/537,617, filed on Jan. 20, 2004.

(51) Int. Cl.
*A61K 31/202* (2006.01)
*A61K 47/14* (2006.01)
*A61K 31/22* (2006.01)
*A61K 31/232* (2006.01)

(52) U.S. Cl.
CPC ............... *A61K 31/202* (2013.01); *A61K 47/14* (2013.01); *A61K 31/22* (2013.01); *A61K 31/232* (2013.01)
USPC .......................................... 514/675; 424/776

(58) Field of Classification Search
USPC ......................................................... 514/675
See application file for complete search history.

(56) References Cited

U.S. PATENT DOCUMENTS

| | | | |
|---|---|---|---|
| 4,696,916 A | 9/1987 | Yabushita | |
| 5,891,440 A | 4/1999 | Lansky | |
| 6,030,622 A | 2/2000 | Shehadeh | |
| 6,060,063 A | 5/2000 | Lansky | |
| 6,451,439 B2 | 9/2002 | Okamoto | |
| 6,630,163 B1 | 10/2003 | Murad | |
| 2002/0012710 A1 | 1/2002 | Lansky | |
| 2003/0129294 A1 | 7/2003 | Barclay | |
| 2004/0102514 A1 | 5/2004 | Krantis | |
| 2006/0281814 A1 | 12/2006 | Angers | |
| 2010/0004334 A1* | 1/2010 | Jouni et al. ................ | 514/560 |

FOREIGN PATENT DOCUMENTS

| | | |
|---|---|---|
| EP | 1175901 A1 | 1/2002 |
| GB | 758724 | 10/1956 |
| GB | 1466418 | 3/1977 |
| JP | 09-040579 | 2/1997 |
| JP | 2002165559 | 6/2002 |
| JP | 2002176913 A | 6/2002 |
| JP | 2002238566 | 8/2002 |

OTHER PUBLICATIONS

Bassaganya-Riera, J., R. Hontecillas, et al. (2001). "Effects of dietary conjugated linoleic acid in nursery pigs of dirty and clean environments on growth, empty body composition, and immune competence." *J Anim Sci* 79(3): 714-21.
Bassaganya-Riera, J., R. Hontecillas, et al. (2001). "Dietary conjugated linoleic acid modulates phenotype and effector functions of porcine cd8(+) lymphocytes." *J Nutr* 131(9): 2370-7.
Bassaganya-Riera, J., R. Hontecillas, et al. (2002). "Long-term influence of lipid nutrition on the induction of CD8(+) responses to viral or bacterial antigens." *Vaccine* 20(9-10): 1435-44.
Bassaganya-Riera, J., R. M. Pogranichniy, et al. (2003). "Conjugated Linoleic Acid Ameliorates Viral Infectivity in a Pig Model of Virally Induced Immunosuppression." *J Nutr* 133: 3204-3214.
Bassaganya-Riera, J., K. Reynolds, et al. (2004). "Activation of PPAR gamma and delta by conjugated linoleic acid mediates protection from experimental inflammatory bowel disease." *Gastroenterology* 127(3): 777-91.
Camilleri, M. (2003). "GI clinical research 2002-2003: The year in review." *Clinical Gastroenterology and Hepatology* 1: 415-420.
Christie, W.W. (2003). "Fatty Acids: Polyunsaturated With Other Than Methylene-interrupted Double Bonds." Http://www.lipidlibrary.co.uk/Lipids/fa_conj+/ (5 pages).
Hernandez, F., P. Melgarejo, J.M. Olias and F. Artes. "Fatty acid composition and total lipid content of seed oil from three commercial pomegranate cultivars." CIHEAM—Options Mediterraneennes, 205-209, (2000).
Hora, J. J., E. R. Maydew, et al. (2003). "Chemopreventive effects of pomegranate seed oil on skin tumor development in CD1 mice." *J Med Food* 6(3): 157-61.
Hornung, E., C. Pernstich, et al. (2002). "Formation of conjugated Delta11Delta13-double bonds by Delta12-linoleic acid (1,4)-acyl-lipid-desaturase in pomegranate seeds." *Eur J. Biochem* 269(19): 4852-9.
Iwabuchi, M., J. Kohno-Murase, et al. (2003). "Delta 12-oleate desaturase-related enzymes associated with formation of conjugated trans-delta 11, cis-delta 13 double bonds." *J Biol. Chem* 278(7): 4603-10.

(Continued)

*Primary Examiner* — Jeffrey S. Lundgren
*Assistant Examiner* — Meghan Finn
(74) *Attorney, Agent, or Firm* — Daniel A. Blasiole; Charles S. Sara, Esq.; DeWitt Ross & Stevens SC

(57) ABSTRACT

Disclosed is a method of enhancing the immune response of an animal, including mammals and humans, to prevent or ameliorate immunoinflammatory diseases such as Inflammatory Bowel Disease, increase immune system development, maintain or increase $CD4^+$ and $CD8^+$ T lymphocyte levels, increase immune function, increase immune response against viruses and prevent or ameliorate the Metabolic Syndrome, Type 2 diabetes and obesity by administering orally or parenterally a therapeutically effective amount of punicic acid to the animal.

19 Claims, 6 Drawing Sheets

(56) References Cited

OTHER PUBLICATIONS

Kim, N. D., R. Mehta, et al. (2002). "Chemopreventive and adjuvant therapetuic potential of pomegranate (*Punica granatum*) for human breast cancer." *Breast Cancer Research and Treatment* 71: 203-207.

Lichtenstein, G. R., M. Abreu, et al. (2003). Recent advances in the treatment of Crohn's colitis, The center for health care education, LLC.

Moller, D. E. and J. P. Berger (2003). "Role of PPARs in the regulation of obesity-related insulin sensitivity and inflammation." *Int J Obes Relat Metab Disord* 27 Suppl 3: S17-21.

Rubins, H. B. and S. J. Robins (2000). "Conclusions from the VA-HIT study." *Am J Cardiol* 86(5): 543-4.

Saubermann, L. J., P. Beck, et al. (2000). "Activation of natural killer T cells by alpha-galactosylceramide in the presence of CD1d provides protection against colitis in mice." *Gastroenterology* 119(1): 119-28.

Schubert, S.Y., E.P. Lansky and I. Neeman (1999). "Antioxidant and eicosanoid enzyme inhibition properties of pomegranate seed oil and fermented juice flavonoids." *Journal of Ethnopharmacology* 66: 11-17.

Sharaf, A., and S.A.R. Nigm (1964). "Short Communications, The Oestrogenic Activity of Pomegranate Seed Oil." *J. Endocrin.* 29: 91-92.

Strober, W., I. J. Fuss, et al. (2002). "The immunology of mucosal models of inflammation." *Annu Rev Immunol* 20: 495-549.

Suzuki, R., R. Noguchi, T. Ota, M. Abe, K. Miyashita and T. Kawada (2001). "Cytotoxic Effect of Conjugated Trienoic Fatty Acids on Mouse Tumor and Human Monocytic Leukemia Cells." *Lipids*, vol. 36, No. 5: 477-482.

Vohl, M. C., R. Sladek, et al. (2004). "A survey of genes differentially expressed in subcutaneous and visceral adipose tissue in men." *Obes Res* 12(8): 1217-22.

* cited by examiner

METHOD OF USING PUNICIC ACID TO ENHANCE IMMUNE RESPONSE AND PREVENT METABOLIC DISORDERS

CROSS-REFERENCE TO RELATED APPLICATIONS

This application is a continuation of U.S. patent application Ser. No. 12/710,906 filed Feb. 23, 2010, which is a divisional application of U.S. patent application Ser. No. 11/039,419 filed Jan. 20, 2005, which is a continuation-in-part of U.S. patent application Ser. No. 11/031,591 filed Jan. 7, 2005, which claims priority under 35 U.S.C. §119(e) to U.S. Provisional Patent Application 60/537,617 filed Jan. 20 2004, all of which are incorporated herein by reference in their entirety.

FIELD OF THE INVENTION

The present invention is generally directed to a method of using punicic acid to enhance the immune response, while minimizing the adverse side effects of immune activation and preventing immunoinflammatory or metabolic disorders in animals, including mammals and humans. More specifically, a method is provided using punicic acid to enhance immune response, increase immune system development, prevent or ameliorate immunoinflammatory and metabolic disorders (i.e., Metabolic Syndrome, obesity and type 2 diabetes), maintain or increase CD4$^+$ and CD8$^+$ T cell levels, and improve resistance to viral diseases.

CITED REFERENCES

A full bibliographic citation of the references cited in this application can be found in the section preceding the claims.

DEFINITIONS

The following definitions are used throughout the present application:

Antigen: Any substance that may be specifically bound by an antibody molecule or T cell receptor.

ANOVA: Analysis of variance. An arithmetic process for partitioning the overall variation in data sets into specific components based on sources of variation. It has been used to determine whether numerical differences between treatment groups are statistically significant.

Adipogenesis: the process by which new adipocytes or fat storage cells are generated.

CD19: Cluster Differentiation 19. A protein expressed on the surface of B cells.

CD4: Cluster Differentiation 4. A co-receptor found on the surface of helper T cells.

CD3: Cluster Differentiation 3. A co-receptor found on the surface of all T cells.

CD8: Cluster Differentiation 8. A co-receptor found on the surface of cytotoxic T cells.

CD4$^+$ T cells: Helper T cells. Cells that secrete proteins that modulate the activity of other immune cells against antigens.

CD8$^+$ T cells: Cytotoxic T cells. Cells capable of disabling or destroying abnormal cells, including tumor cells, virus-infected cells and cells infected with intracellular bacteria.

ConA: Concanavalin A. A mitogen that induces proliferation of lymphocytes. Stimulation of lymphocytes with ConA has been widely utilized to examine the effects of dietary interventions on immune function.

cRPMI: Complete Roswell Park Memorial Institute media. A cell culture media formulated to contain all the nutrients necessary for long-term cell survival. Detailed composition shown under media and reagent preparation.

DSS: Dextran Sodium Sulfate. A chemical administered by drinking water (2.5% wt/v) to cause the death of the epithelial cells of the colon and induce colonic inflammation. The DSS colitis model is a well-established model of experimental IBD.

Epitope: A part of an antigen presented in the major histocompatibility complex 1 or 2 that is recognized specifically either by an antibody or by the T cell receptor.

FACS: Fluorescence-Activated Cell Sorting. A special buffer used for flow cytometry applications to prevent the internalization of cell surface markers. Detailed composition shown under media and reagent preparation.

Glycemia: Concentration of glucose in blood.

Hyperglycemia: Increased concentration of glucose in blood beyond normal ranges.

Hyperinsulinemia: Increased concentrations of insulin in blood beyond normal ranges.

IBD: Inflammatory Bowel Disease. An immunoinflammatory disease of the intestine characterized by two clinical manifestations—Crohn's Disease (CD) and Ulcerative Colitis (UC).

Insulinemia: Concentration of insulin in blood.

mAb: Monoclonal antibody. An antibody produced by B cells in response to specific antigenic stimulation that binds to specific regions of a protein.

Nutraceutical: A compound with specific medicinal as well as nutritional benefits.

PBS: Phosphate-Buffered Saline. A buffer used in cell culture applications. Cells can be resuspended in PBS for short periods of time before transfer to a more nutritious buffer. Detailed composition shown under media and reagent preparation.

TCR: T-Cell Receptor. A protein expressed on the surface of T lymphocytes, which is always co-expressed with the CD3 molecule that recognizes specific antigens. Following antigen recognition, it activates the lymphocyte and initiates an immune response against the antigen.

Type 2 diabetes or Non-insulin dependent Diabetes Mellitus: The more common type of diabetes caused by an unresponsiveness of cells to the actions of insulin. If cells do not respond to insulin, they are unable to take up glucose from blood, which results in glucotoxicity. In addition, the cells are deprived from the energy derived from glucose oxidation.

DESCRIPTION OF THE PRIOR ART

The immune response is the body's mechanism of defense against foreign substances that invade to cause infection and/or disease. The immune system's functions are complicated processes that involve the coordinated efforts of several types of cells, including white blood cells. The immune response begins when an antigen-presenting cell encounters a foreign antigen. The antigen-presenting cell degrades it and displays pieces of the antigen (i.e., a virus, bacteria or other foreign body) called epitopes on its surface.

Unique among the many different clones of T cells (a subpopulation of white blood cells) in the body, one particular T cell clone recognizes the antigen displayed and binds to the antigen-presenting cell. This union modulates the production of proteins called cytokines by the antigen-presenting cell, such as interleukin-1 (IL-1) and tumor necrosis factor (TNF). These proteins communicate between the antigen-presenting cell and T cell. The T cell also produces other proteins such as interleukin-2 (IL-2) and gamma interferon (IFN-γ). As part of the continuing process, IL-2 instructs other T cells and killer T cells to multiply.

The proliferating helper T cells release substances that cause B cells to multiply and produce antibodies. The antibodies released by the B cells bind to antigens on the surfaces of free-floating viruses and other pathogens. As the infection is brought under control, the activated T and B cells are turned off by suppressor T cells. However, a few "memory cells" remain behind to respond quickly if the same pathogen attacks again.

Due to the complexity of the body's immune response, further study is needed to reveal novel ways to bolster the immune system to enhance the immune response of an animal. Ideally, new methods of enhancing the immune system will act to prevent or attenuate the adverse side effects associated with immune and/or inflammatory responses.

Current research also indicates that other immune disorders such as Inflammatory Bowel Disease (IBD) may also be helped by further research into the immune system. IBD is a chronic, recurring immunoinflammatory illness of unknown etiology afflicting over 1,000,000 Americans and several million people worldwide. IBD is a prevalent cause of chronic illness in a large segment of the patient population. It can manifest itself in two different forms: Ulcerative Colitis (UC) and Crohn's Disease (CD). Although the two conditions clinically appear very similar, UC primarily involves inflammation of the colon and rectum, as opposed to the upper gastrointestinal tract. CD, on the other hand, impacts a greater area of the upper intestinal digestive tract, and is thus more likely to trigger malabsorption and chronic vitamin and nutrient deficiencies.

Individuals suffering from IBD experience symptoms characterized by chronic intestinal inflammation, diarrhea, bleeding, abdominal pain, fever, joint pain, and weight loss. These symptoms can range from mild to severe. IBD may gradually and subtly develop from an initial minor discomfort, or may present suddenly with acute intensity.

Current treatments for IBD include corticosteroids such as 6-methylprednisolone and budesonide, and immunosuppressives such as azathioprine, 6-mercaptopurine, cyclosporine, and methotrexate (Lichtenstein et al. 2003). New therapies still under development include the Food and Drug Administration-approved anti-tumor necrosis factor (TNF-α) (Camilleri 2003; Lichtenstein et al. 2003; Bassaganya-Riera et al. 2004). While existing therapies against IBD have improved, they remain only modestly successful. Further, conventional therapies often result in significant side effects to the user. Therefore, there remains a need for novel preventive and/or therapeutic methods for treating immunoinflammatory diseases such as IBD.

There also remains a need for novel methods of enhancing immune response in a mammal using nutritional products. Further research into the immune system may identify nutritional interventions that prevent immune suppression.

A need also exists for novel methods of enhancing the immune response in immunosuppressed individuals such as babies, children and the elderly. These individuals have a limited ability to respond to viral and bacterial infections, resulting in decreased resistance against viral and bacterial disease. Therefore, there remains a need to identify novel methods of enhancing the immune response of these vulnerable individuals, including nutritional methods. A need also exists for novel methods of treating or preventing metabolic disorders such as the Metabolic Syndrome or Syndrome X and Type 2 diabetes. In western societies, the high prevalence of obesity results in several metabolic disorders such as Type 2 diabetes, cardiovascular disease, hypertension, and hyperlipidemia, which are all characterized as Syndrome X. Approximately 15 million Americans are afflicted by Type 2 diabetes, with 1 million newly diagnosed cases and $132 billion in medical expenses per year. Some components of Metabolic Syndrome (such as insulin resistance and obesity) appear to be associated with immunoinflammatory abnormalities. This connection between immunity, inflammation and metabolism is particularly strong in the abdominal adipose tissue. Vohl et al. demonstrated that the expression of pro-inflammatory cytokines and their receptors (i.e., IL-6 and IL-1R) was increased in human omental adipose tissue when compared with subcutaneous adipose tissue (Vohl et al. 2004). Gemfibrozil, an agonist of peroxisome proliferator-activated receptor alpha, is approved for the treatment of cardiovascular disease and elicits cardioprotective effects that cannot be fully explained by its effects on blood lipid profiles (Rubins et al. 2000; Moller et al. 2003). Hence, other mechanisms are also implicated in improving cardiovascular disease. Modulation of immune function and inflammation by gemfibrozil provides an explanation for its potent health benefits. Additionally, gemfibrozil is an example of a successful intervention against a metabolic disorder using an approach that acts on metabolism but also on immune function and inflammation.

Novel treatments for Type 2 diabetes include agonists of peroxisome proliferator-activated receptor gamma such as thiazolidinediones (TZDs). However, questions have been raised regarding the safety of these treatments due to adverse cardiovascular (fluid retention and congestive heart failure) and liver (fatty liver) side effects. Therefore, there remains a need to identify novel and safer methods of preventing or treating Metabolic Syndrome, Type 2 diabetes and obesity, including nutritional methods that act upon molecular networks located in the interface between immunity, inflammation and metabolism.

One such novel and safe method may be treatment with punicic acid. Punicic acid is a non-toxic, natural, orally active food ingredient known to humans and consumed by humans for centuries. Punicic acid is naturally found in seeds of pomegranate, i.e., *Punica granatum*, representing over 60 percent of the oil. *Momordica balsamina* is another medicinal plant belonging to the cucumber family with a similar concentration of punicic acid. The presence of punicic acid in pomegranate seeds and other medicinal plants is well-known in the field. Also, the benefits of pomegranates against cancer are well known in the field. For instance, methods of treating medical disorders using the pomegranate fruit are common. However, methods of enhancing immune response in mammals using punicic acid are not. For instance, U.S. Pat. No. 6,630,163 to Murad teaches a method of treating dermatological disorders with fruit extracts, including pomegranate. The method includes administering therapeutically effective amounts of at least one fruit extract to neutralize free radicals in the skin. This method is aimed at targeting and curing disorders in the skin. However, this method does not teach the use of pomegranate oil or punicic acid to enhance the immune response as a method of treating disorders in the immune system and gastrointestinal tract. In addition, the use of punicic acid to promote the development and function of the immune system or prevention of metabolic disorders is also not taught.

U.S. Pat. No. 6,030,622 to Shehadeh teaches a method of preparing an herbal extract composition comprising extract of arum, extract of pomegranate, extract of tea and extract of hibiscus. The components of the pomegranate used to create the extract are fruit peels, but fruit peels do not contain punicic acid (which is only found in the seed.) In addition, the methods of extraction utilized (aqueous and ethanolic) are designed to extract hydrosoluble components, not the oil or the punicic acid.

Further, U.S. Pat. Nos. 6,060,063 and 5,891,440 to Lansky teach a method of preparing a phytoestrogen oral supplement and ointment by extracting pomegranate seeds with an aqueous solvent and admixing the pomegranate seed extract with an herbal extract containing shizandra berries, Chinese asparagus root, and optionally Chinese licorice and Chinese angelica root. However, this method does not teach the use of punicic acid to enhance immune response to prevent metabolic disorders in mammals.

Japanese Patent 2002238566 to Murase and Imamura teaches a method of cloning the gene involved in the synthesis of catalpic and punicic acid. While this technology may be useful for the enzymatic production of punicic acid, it does not teach the use of punicic acid to enhance a mammal's immune response or to prevent metabolic disorders.

Other patents, such as Great Britain Patents 1466418 and 758724, teach methods of polymerizing conjugated trienoic fatty acids or esters and improving synthetic resins using punicic acid. However, neither patent teaches the medicinal effects of punicic acid on the immune system.

Further, while the use of pomegranate seed oil has been shown to be useful against the proliferation and survival of human breast adenocarcinoma (MCF-7) cells, only in-vitro studies using topical administrations have been completed (Kim et al. 2002). Other studies have shown the use of pomegranate oil to be effective in the treatment of tumors in a mouse model of chemically induced skin cancer (Hora et al. 2003).

SUMMARY OF THE INVENTION

In response to the above-described needs, the present invention provides a method of enhancing the immune response of an animal, including mammals and humans, in need thereof. The method comprises administering a therapeutically effective amount of a compound selected from the group consisting of punicic acid, esters thereof, pharmaceutically suitable salts thereof, metabolites thereof, and combinations thereof. The compound may be administered to the animal in a single dose or a multiple dose. This method utilizes the natural qualities of punicic acid to enhance the immune response of an animal, including mammals and humans.

The method provided herein shows that punicic acid may be used as a preventative or therapeutic compound to enhance immune response and treat immunoinflammatory (i.e., IBD, allergies and autoimmune diseases) and metabolic disorders (i.e., obesity and Type 2 diabetes). Punicic acid also shows promise in adjunct therapies aimed at further enhancing the efficacy of other pharmacologic treatments currently utilized to prevent or ameliorate IBD.

Therefore, a method of treating immune disorders in an animal is provided, wherein an amount of punicic acid compound effective to treat the immune disorder is administered to the animal. While any form of punicic acid may be used, in a preferred embodiment, the free acid form of punicic acid is used.

In a preferred embodiment of the present invention, the punicic acid compound is administered orally to the animal. The punicic acid compound may be administered alone or in combination with a pharmaceutically suitable carrier.

The punicic acid compound may also be administered parenterally, via injection or rectally. The punicic acid compound may be administered alone or in combination with a pharmaceutically suitable excipient.

In another embodiment of the present invention, a therapeutically effective amount of the punicic acid compound is administered to an animal in combination with a nutritional food supplement. Such supplements include but are not limited to infant formulas, children products, geriatric formulas, milk, cheese, kefir, cereal bars, weight management formulas, energy bars, other human foods, functional foods, and animal feed.

Punicic acid may also be administered in combination with other active ingredients such as vitamins or other fatty acids.

The effective amount of the punicic acid compound depends on the needs of the animal. For instance, in one embodiment, an amount effective to enhance immune response in an animal is provided.

In another embodiment, an amount of punicic acid compound effective to enhance immune response against viral antigens, specifically influenza antigens, is administered to the animal.

In another embodiment, an amount of punicic acid compound effective to enhance the development of the immune system of an animal is administered. The amount of punicic acid is preferably effective to enhance the development of primary and secondary lymphoid organs and immune cells, including but not limited to the thymus, spleen, lymph nodes, gut-associated lymphoid tissue in the intestine, and other mucosal surfaces.

In another embodiment, an amount of punicic acid compound effective to treat Inflammatory Bowel Disease (IBD) is administered to the animal. Specifically, an amount effective to prevent or ameliorate the clinical signs and intestinal lesions associated with IBD is administered.

In another embodiment, an amount of punicic acid compound effective to treat Type 2 diabetes and obesity is administered to the animal. Specifically, an amount effective to normalize impaired glucose tolerance, prevent hyperglycemia, prevent hyperinsulinemia, and minimize abdominal fat accumulation is administered.

In yet another embodiment, an amount of punicic acid compound effective to increase $CD4^+$ and $CD8^+$ T lymphocyte levels in an animal is administered. The amount of punicic acid compound is preferably effective to increase T cell levels while preventing exacerbated immune responses, allergies, hypersensitivity reactions, or autoimmune reactions.

In another embodiment, an amount of punicic acid compound effective to prevent immunosuppression in an animal, including mammals and humans, is administered to the animal. Specifically, an amount effective to prevent immunosuppression in infants, children, the elderly and other at-risk populations is administered.

The invention also provides a method of preventing or treating a viral and/or a bacterial infection in a mammalian subject comprising the step of administering a safe and effective amount of punicic acid orally or parenterally. Preferably, the method comprises increasing immune function, thereby treating the viral and/or bacterial infection by increasing the immune function of the subject.

Also provided by the invention is the use of a punicic acid in the manufacture of a composition for preventing or treating a viral and/or a bacterial infection, preferably comprising increasing immune function in a subject.

The invention also provides the use of a punicic acid in the manufacture of a composition for preventing or ameliorating an intestinal immune or inflammatory disorder.

Further aspects of the invention are the use of a punicic acid in the manufacture of a composition for increasing immune system development, the use of punicic acid in the manufacture of a medicament for increasing immune function and punicic acid for use in preventing or treating a viral and/or a bacterial infection, preventing or ameliorating an intestinal immune or inflammatory disorder, increasing immune system development or increasing immune function.

The invention also provides a method of improving the nutritional quality of infant formulas, geriatric formulas, milk, cheese, kefir, cereal bars, weight management formulas, other human foods and animal feed, comprising the step of adding a safe and effective dose of punicic acid in the formula's composition.

The formulations of punicic acid disclosed in the present invention may be conveniently presented in unit dosage form and may be prepared by any methods well known in the art of pharmacy or nutrition. Possible formulations include but are not limited to capsules, cachets, tablets, boluses or lozenges, each containing a predetermined amount of punicic acid.

Advantageously, there is no upper limit to the amount of punicic acid that may be administered to an animal in need thereof. Further, the method of the present invention may be administered to animals, including mammals and humans, of all ages and health. For instance, vulnerable populations such as the elderly, obese, diabetic, sick or very young can benefit from the present invention, as can healthy individuals with no history of immunosuppression. In addition, the method of the present invention may be administered in a variety of ways, thereby providing a versatile and efficient means of enhancing the immune response and preventing metabolic disorders in a mammal.

The scope of the invention will appear more fully from the following detailed description of the preferred embodiment of the invention made in conjunction with the accompanying drawings.

DETAILED DESCRIPTION OF THE INVENTION

Punicic Acid

Figure 1A:
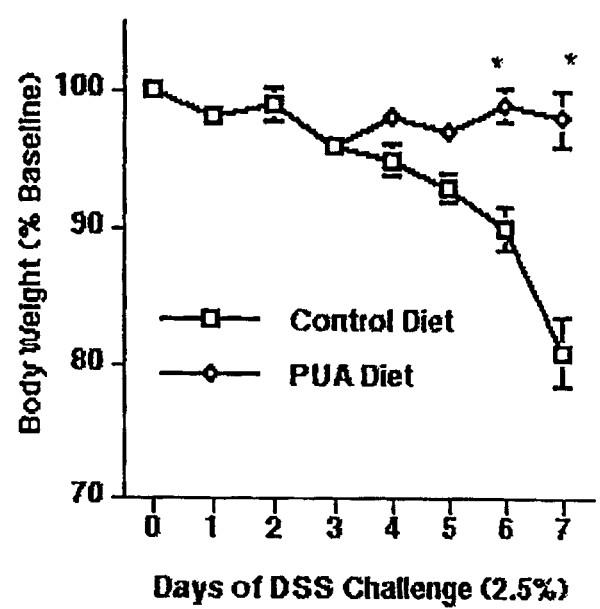
FIG. 1A is a graph illustrating the effects of dietary punicic acid and an isocaloric control diet on body weight losses during Experiment 1.

The term punicic acid, as used herein, refers to a conjugated linolenic acid isomer containing cis-9, trans-11, cis-13 double bonds in the $C_{18}$ carbon chain, its non-toxic salts, active esters, active isomers, active metabolites, structural lipids containing punicic acid, and mixtures thereof. Punicic acid is also known as trichosanic acid and is found in the seed oil of *Punica granatum* (Punicaceae, Pomegranate) and *Trichosanthes anguina* (Cucurbitaceae, snake gourd). Punicic acid constitutes approximately 86% of the oil of the pomegranate seed. Non-toxic salts include, for example, alkyl esters having from 1 to 6 carbon atoms in the alkyl group, as well as mono-, di- and tri-glycerides, and mixtures thereof. Active isomers of punicic acid include geometrical isomers such as eleostearic acid (cis-9, trans-11, trans-13 octadecatrienoic acid) and its non-toxic salts (e.g., sodium, potassium, calcium and magnesium salts) and its active esters (e.g., alkyl esters having from 1 to 6 carbon atoms in the alkyl group), as well as mono-, di- and tri-glycerides, and mixtures thereof.

The punicic acid may be a substantially pure single chemical compound or a mixture of one or more punicic acid compounds as defined above. The term "substantially pure" means having a purity of at least 90% by weight, preferably at least 95% by weight, such as at least 98%, and more preferably still about 99% and 100% by weight. The punicic acid may be in the form of an extract obtainable or obtained from pomegranate seed oil, either directly or following one or more steps of purification.

Punicic acid has an extremely strong ability to resist the oxidizing, inflammation and destruction functions of the free radical of oxygen. Punicic acid has been shown to prevent scleratheroma as well as to delay the progression of cancer in the body. Punicic acid acts physiologically as an antioxidant to lower plasma cholesterol. Further, punicic acid has an inhibitory effect in vitro on aggregation and arachidonic acid metabolism in human platelets. In short, punicic acid has wide application prospects in medicines and health protection, food, and cosmetics industry, to name just a few.

The punicic acid used in the described methods may be in a free acid form or bound chemically through ester linkages. In its natural form, punicic acid is heat stable. Punicic acid may be used in its natural oil state or in a dried and powdered form. Further, the free acid form of punicic acid may be converted into a non-toxic salt, such as sodium, potassium or calcium salts, by reacting chemically equivalent amounts of the free acid form with an alkali hydroxide at a basic pH.

Administration

In the course of the method of the present invention, a therapeutically effective amount of punicic acid compound is administered to an animal, including mammals and humans. While in the preferred embodiment, the punicic acid compound is administered orally or parenterally, other forms of administration such as through medical compounds or aerosols are also contemplated.

For oral administration, an effective amount of punicic acid may be administered in, for example, a solid, semi-solid, liquid or gas state. Specific examples include tablet, capsule, powder, granule, solution, suspension, syrup, and elixir agents. However, the punicic acid compound is not limited to these forms.

To formulate the punicic acid of the present invention into tablets, capsules, powders, granules, solutions or suspensions, the punicic acid compound is preferably mixed with a binder, a disintegrating agent and/or a lubricant. If necessary, the resultant composition may be mixed with a diluent, a buffer, an infiltrating agent, a preservative and/or a flavor, using known methods. Examples of the binder include crystalline cellulose, cellulose derivatives, cornstarch, and gelatin. Examples of the disintegrating agent include cornstarch, potato starch, and sodium carboxymethylcellulose. Examples of the lubricant include talc and magnesium stearate. Further, additives such as lactose and mannitol, may also be used.

For parenteral administration, the punicic acid compound of the present invention may be administered rectally or by injection. For rectal administration, a suppository may be used. The suppository may be prepared by mixing the punicic acid of the present invention with a pharmaceutically suitable excipient that melts at body temperature but remains solid at room temperature. Examples include but are not limited to cacao butter, carbon wax or polyethylene glycol. The resulting composition may be molded into any desired form using methods known to the field.

For administration by injection, the punicic acid compound of the present invention may be injected hypodermically, intracutaneously, intravenously or intramuscularly. Medicinal drugs for such injection may be prepared by dissolving, suspending or emulsifying the punicic acid of the invention into an aqueous or non-aqueous solvent such as vegetable oil, glyceride of synthetic resin acid, ester of higher fatty acid, or propylene glycol by a known method. If desired, additives such as a solubilizing agent, an osmoregulating agent, an emulsifier, a stabilizer, or a preservative may also be added.

For formulating the punicic acid of the present invention into suspensions, syrups or elixirs, a pharmaceutically suitable solvent may be used.

The punicic acid compound of the present invention may also be used together with an additional compound having other pharmaceutically suitable activity to prepare a medicinal drug.

The punicic acid of the present invention may also be administered in the form of an aerosol or inhalant prepared by charging the punicic acid in the form of a liquid or fine powder, together with a gaseous or liquid spraying agent and, if necessary, a known auxiliary agent such as an inflating agent, into a non-pressurized container such as an aerosol container or a nebulizer. A pressurized gas of, for example, dichlorofluoromethane, propane or nitrogen may be used as the spraying agent.

Punicic acid may be administered to an animal, including mammals and humans, in need thereof as a pharmaceutical or veterinary composition, such as tablets, capsules, solutions or emulsions. In a preferred embodiment of the invention, the free acid form of punicic acid is administered. However, administration of other forms of punicic acid, including but not limited to esters thereof, pharmaceutically-suitable salts thereof, metabolites thereof, and combinations thereof, in a single dose or a multiple dose, are also contemplated by the present invention.

Punicic acid may also be administered to an animal in need thereof as a nutritional additive, either as a food or nutraceutical supplement.

The terms "preventing or treating", "treating or ameliorating" and similar terms used herein, include prophylaxis and full or partial treatment. The terms may also include reducing symptoms, ameliorating symptoms, reducing the severity of symptoms, reducing the incidence of the disease, or any other change in the condition of the patient which improves the therapeutic outcome.

The punicic acid is preferably used and/or administered in the form of a composition. Suitable compositions are, preferably, a pharmaceutical composition, a foodstuff or a food supplement. These compositions provide a convenient form in which to deliver the punicic acid. Compositions of the invention may comprise an antioxidant in an amount effective to increase the stability of the punicic acid with respect to oxidation.

The amount of punicic acid administered is preferably from about 0.001 g to about 20 g (more preferably 0.1 g to 10 g, such as 0.5 g to 5 g) of punicic acid or derivative thereof per day. Suitable compositions can be formulated accordingly.

A preferred composition according to the invention is a foodstuff. Food products (which term includes animal feed) preferably contain a fat phase, wherein the fat phase contains punicic acid. The foodstuffs are optionally used as a blend with a complementary fat. For example, the blend may comprise 0.3-95 wt %, preferably 2-80 wt %, most preferably 5-40 wt % of punicic acid; and 99.7-5 wt %, preferably 98-20 wt %, most preferably 95-60 wt % of a complementary fat such as cocoa butter, cocoa butter equivalents, palm oil or fractions thereof, palm kernel oil or fractions thereof, interesterified mixtures of said fats or fractions thereof; or liquid oils such as sunflower oil, high oleic sunflower oil, soybean oil, rapeseed oil, cottonseed oil, fish oil, safflower oil, high oleic safflower oil and maize oil. Examples of suitable foodstuffs include those selected from the group consisting of margarines, fat continuous or water continuous or bicontinuous spreads, fat reduced spreads, confectionery products such as chocolate or chocolate coatings or chocolate fillings or bakery fillings, ice creams, ice cream coatings, ice cream inclusions, dressings, mayonnaises, cheeses, cream alternatives, dry soups, drinks, cereal bars, sauces, snack bars, dairy products, clinical nutrition products and infant formulations.

Other examples of compositions are pharmaceutical compositions, such as in the form of tablets, pills, capsules, caplets, multiparticulates including: granules, beads, pellets and micro-encapsulated particles; powders, elixirs, syrups, suspensions and solutions. Pharmaceutical compositions may comprise a pharmaceutically acceptable diluent or carrier and are preferably adapted for parenteral administration (e.g., orally). Orally administrable compositions may be in solid or liquid form and may take the form of tablets, powders, suspensions and syrups. Optionally, the compositions may comprise one or more flavoring and/or coloring agents.

Pharmaceutically acceptable carriers suitable for use in such compositions are well known in the art of pharmacy. The compositions of the invention may contain 0.1-99% by weight of punicic acid. The compositions of the invention are generally prepared in unit dosage form. Preferably the unit dosage of punicic acid is from 1 mg to 1000 mg (more preferably from 100 mg to 750 mg). The excipients used in the preparation of these compositions are the excipients known in the art.

Further examples of product forms for the composition are food supplements, such as in the form of a soft gel or a hard capsule comprising an encapsulating material selected from the group consisting of gelatin, starch, modified starch, starch derivatives such as glucose, sucrose, lactose and fructose. The encapsulating material may optionally contain cross-linking or polymerizing agents, stabilizers, antioxidants, light absorbing agents for protecting light-sensitive fills, preservatives and the like. Preferably, the unit dosage of punicic acid in the food supplements is from 1 mg to 1000 mg (more preferably from 100 mg to 750 mg).

The method of the present invention administers a therapeutically effective amount of punicic acid compound to an animal in need thereof. The effective amount of punicic acid depends on the form of punicic acid compound administered, the duration of the administration, the route of administration (e.g., oral or parenteral), the age of the animal and the condition of the animal.

For instance, an amount of punicic acid effective to enhance immune response in an animal ranges from 10 to 10,000 mg/kg/day. A preferred effective amount of punicic acid is 100 to 5,000 mg/kg/day, with a more preferred dose being 10 to 100 mg/kg/day. An effective amount of approximately 35 to 40 mg/kg/day of punicic acid is also envisioned by the method of the present invention, with 38 mg/kg/day the preferred dose. The upper limit of the effective amount to be administered is not critical, as punicic acid is relatively non-toxic as long as the recipient's diet contains the necessary essential fatty acids.

An amount of punicic acid effective to treat and prevent IBD, including UC and CD can range from 50 to 500 mg/kg/day, with a preferred dose of 100 to 150 mg/kg/day.

The effective amount of punicic acid is most effective in enhancing the immune response of an animal when administered for periods ranging from about 7 to 100 days, with a preferred period of 15 to 50 days, and a most preferred period of 30 to 42 days.

An amount of punicic acid most effective in preventing and treating Type 2 diabetes and obesity can range from 40 to 500 mg/kg/day, with a preferred dose of 100 to 150 mg/kg/day.

When the effective amount of the punicic acid compound of the present invention is administered in a nutritional, medical or veterinary composition, the preferred dose ranges from about 0.01 to 2.0% wt/wt to the food or nutraceutical product.

The invention may involve the treatment of bacterial or viral infections or of diseases or disorders caused by bacterial or viral infections. Examples of bacterial infections include, for example, infections caused by microorganisms from the genus *Staphylococcus, Aeromonas, Legionella, Bacillus* or *Micrococcus*, including, but not limited to, *Staphylococcus aureus, Aeromonas hydrophila, Legionella pneumophila* or *Bacillus laterosporus*. Viral infections include, for example, those caused by one of the following: Picornavirus, Togavirus, Paramyxovirus, Orthomyxovirus, Rhabdovirus, Reovirus, Retrovirus, Bunyavirus, Coronavirus, Arenavirus, Parvoviruses, Papovavirus, Adenovirus, Herpevirus and Poxvirus.

Examples of a disease or disorder in which the immune system is deficient include, for example, diseases or disorders resulting from treatment with drugs (such as in chemotherapy), malnutrition and infection (e.g., with a virus such as HIV and AIDS).

Preparation of Punicic Acid

Punicic acid-enriched pomegranate oil has been previously isolated from pomegranate seeds and described as an anticarcinogen (Kim et al. 2002; Hora et al. 2003). Pomegranate seeds were separated from their juice sacks, washed in water and dried in a convection dryer. Oil extrusion was performed by "cold press" at 80° C., using a Type 40A electric screw press (Skeppsta Maskin, Orebro, Sweden). The resulting oil contained 480 mg of punicic acid per gram of oil. Punicic acid can also be obtained by enzymatic biosynthesis through methods known in the field (Iwabuchi et al. 2003, Hornung et al. 2002).

However, because enzymatic synthesis and cold press methods of punicic acid extraction are inefficient (e.g., 10% yield), solvent extraction methods are recommended. Before solvent extraction, seeds are steam-heated to reduce enzymatic hydrolysis and improving processing. After heating, seeds are finely ground and used in a solvent extraction. Regular liquid solvents such as hexane require soaking the seeds multiple times for up to 12 to 20 hours with stifling, filtering, and solvent evaporation. Alternatively, punicic acid-enriched pomegranate oil may be generated by $CO_2$ super critical extraction methods known to the art.

Because the oil is more susceptible to oxidative processes when released from the seed, extraction is preferably performed under a nitrogen blanket to prevent contact with the air. Additionally, the oil is nitrogen-purged and stored with one or various antioxidants in the dark at 4° C. or at −20° C. for longer-term storage. Oil from pomegranate seeds is expressed during this process in an amount by weight of 18% of the weight of the seeds.

The practice of the present invention is further illustrated by the following experiments. All publications, patents and patent applications referenced in the Experiments section are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The following non-limiting examples illustrate the invention and do not limit its scope in any way. In the examples and throughout this specification, all percentages, parts and ratios are by weight unless indicated otherwise.

Experiments

Experiment 1

Objective To determine the effect of punicic acid on IBD and colitis-associated disease.

Methods

In the first experiment, eleven (11) C57BL6 mice were fed zero or 0.6 g punicic acid/100 g food (1% pomegranate oil) for thirty-eight (38) days. The diets were made isocaloric by replacing (wt/wt basis) punicic acid with linoleic acid in the control diet. On day 32 of the experiment (seven days prior to sacrificing the mice), intestinal inflammation was induced by challenging mice with 2.5% DSS, 36,000 to 44,000 mol/wt (ICN Biomedicals, Aurora, Ohio) in the drinking water. Animal models of IBD, including the DSS colitis model represent a means to probe the immunological pathogenesis of IBD (Strober et al. 2002) and a safe method of testing the preventive and/or therapeutic efficacy of novel compounds, such as punicic acid. One of the key features of the DSS challenge is its ability to disrupt the epithelial cell barrier and promote increased cellular exposure to normal luminal and mucosal microflora (Strober et al. 2002). Following the DSS challenge, mice were weighed on a daily basis and examined for clinical signs of disease associated with colitis (i.e., perianal soiling, rectal bleeding, diarrhea, and piloerection) by blinded observers. The disease activity indices and rectal bleeding scores were calculated using a previously published compounded clinical score (Saubermann et al. 2000; Bassaganya-Riera et al. 2004).

After the mice were sacrificed, the colons, brains, kidneys, livers and spleens were harvested from the mice. The colons were weighed and scored by blinded observers based on the severity of macroscopic lesions following a scale on 0 to 3 (e.g., 0=no lesions and 3=severe lesions). Colonic contents were washed by gently rinsing the colon with sterile 1×PBS using a mouse gavage needle connected to a 5 mL syringe. The other tissues were directly added to the formalin beaker. All specimens were generally labeled with the following information: 1) mouse number; 2) date collected; 3) experiment number; 4) type of solvent; and 5) tissue type. Sections of colon, brain, kidney and liver were fixed in 10% buffered neutral formalin (Fisher, Atlanta, Ga.), later embedded in paraffin, and then sectioned (6-μm) and stained with the hematoxylin and eosin stain (H&E) (AML Labs, Baltimore, Md.) for histological examination. Tissue slides were examined in an Olympus microscope (Olympus America Inc., Dulles, Va.) and processed in Adobe Photoshop Elements 2.0 (Adobe Systems Inc., San Jose, Calif.).

Colons were graded with a compounded histological score including the extent of 1) crypt damage and 2) regeneration, 3) metaplasia/hyperplasia, 4) lamina proprial vascular changes, 5) submucosal changes and 6) presence of inflammatory infiltrates. The sections were graded with a range from 0 to 4 for each of the previous categories and data was presented as a normalized compounded score. For crypt damage: 0=none; 1=basal ⅓; 2=basal ⅔; 3=only surface epithelium intact; 4=entire crypt and epithelium lost. For epithelial erosion: 0=no erosion; 1=mild focal erosion; 2=mild multifocal erosion; 3=significant ulcers throughout the colon; 4=colonic architecture lost. For mucosal thickness: 0=normal thickness; 1=mild increase in thickness; 2=mild to severe increase in thickness; 3=severe increase in thickness; 4=mucosa obliterating the lumen of the intestine. For regeneration: 4=no tissue repair; 3=surface epithelium not intact; 2=regeneration with crypt depletion; 1=almost complete regeneration; 0=complete regeneration or normal tissue. For metaplasia/hyperplasia: 0=none; 1=mild goblet cell; 2=severe goblet cell metaplasia; 3=goblet cell metaplasia and presence of immature cells in the base and extending to ⅔ of the gland; 4=presence of immature cells in the base and extending beyond ⅔ of the gland. For vascular changes: 0=none; 1=mild capillary dilation in the lamina propria; 2=mild capillary dilation in the lamina propria and submucosa; 3=severe capillary dilation; 4=lamina proprial hemorrhage. For lamina proprial leukocytic infiltrates: 0=normal infiltrate (equal matrix of plasma cells and lymphocytes with some neutrophils); 1=mild increase of neutrophils in lamina propria; 2=mild increase in neutrophils extending towards the submucosa; 3=severe neutrophil homing in the lamina propria and/or submucosa; 4=severe neutrophil homing in the lamina propria and/or submucosa and plasmacytic shift of the lamina propria. Brain, kidney and liver were collected to assess the safety of oral punicic acid administration.

Statistical analysis was performed by analysis of variance (ANOVA). The ANOVA was performed using the general linear model procedure of SAS (SAS 1988) as previously described (Bassaganya-Riera et al. 2003). Differences with probability value (P<0.05) were considered statistically significant.

Results

Figure 1B:
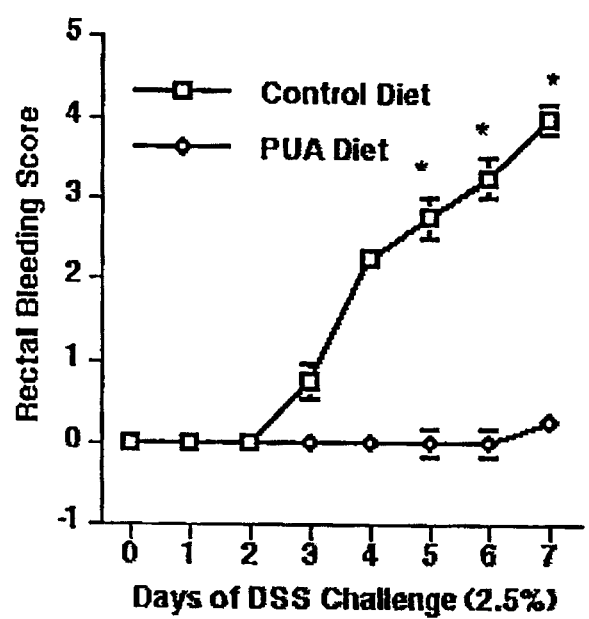
FIG. 1B is a graph illustrating the effects of dietary punicic acid and an isocaloric control diet on rectal bleeding during Experiment 1.
Figure 1C:
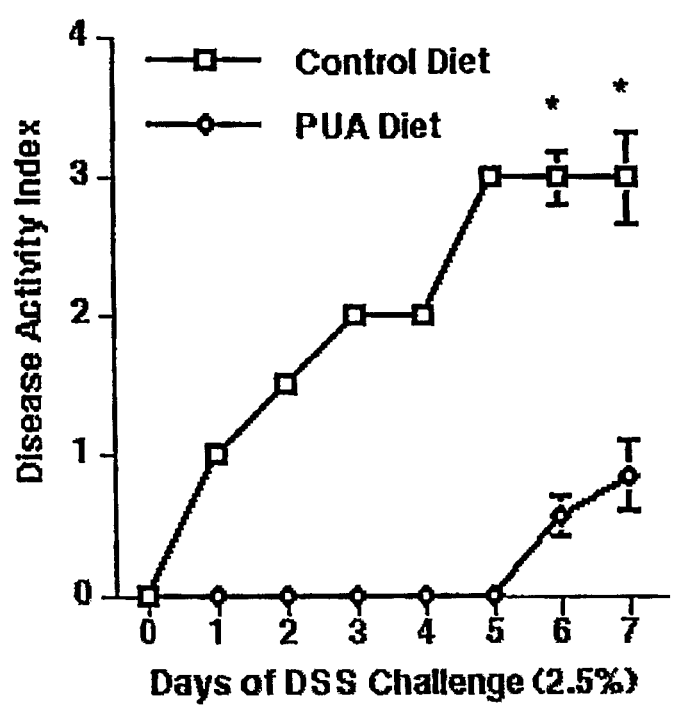
FIG. 1C is a graph illustrating the effects of dietary punicic acid and an isocaloric control diet on disease activity indices during Experiment 1.

The mortality associated with colonic inflammation in the control group was 50% by day 6 of the 2.5% DSS challenge, whereas the mortality rate in punicic acid-fed mice was 0%. The average onset of clinical disease in control mice was 1 day after initiating the DSS challenge; whereas in mice fed the control diet, clinical disease did not appear until 6 days after the DSS challenge. On average, rectal bleeding started on day 4 of the DSS challenge in control-fed mice, whereas it did not start until day 7 of the DSS challenge in mice fed punicic acid-supplemented diets. The DSS challenge induced weight losses, colitis-associated clinical disease and rectal bleeding, which appeared earlier and were more severe in mice fed the control diet than in those fed punicic acid-supplemented diets. FIG. 1A illustrates the effects of dietary punicic acid (0.6 g/100 g) and an isocaloric control diet on body weight losses during a 7-day DSS challenge (2.5%, wt/vol), which is representative of experimentally induced IBD. FIG. 1B illustrates the effects of dietary punicic acid (0.6 g/100 g) and an isocaloric control diet on rectal bleeding during a 7-day DSS challenge (2.5%, wt/vol). FIG. 1C illustrates the effects of dietary punicic acid (0.6 g/100 g) and an isocaloric control diet on disease activity indices during a 7-day DSS challenge (2.5%, wt/vol). Mice were fed a punicic acid-supplemented diet for 32 days prior to the DSS challenge. Colitis-associated disease was improved. The prevention or amelioration of clinical signs of colonic inflammation correlated with lower colon weights in punicic acid-fed mice and less severe scores upon macroscopic analysis of lesions.

Figure 2:
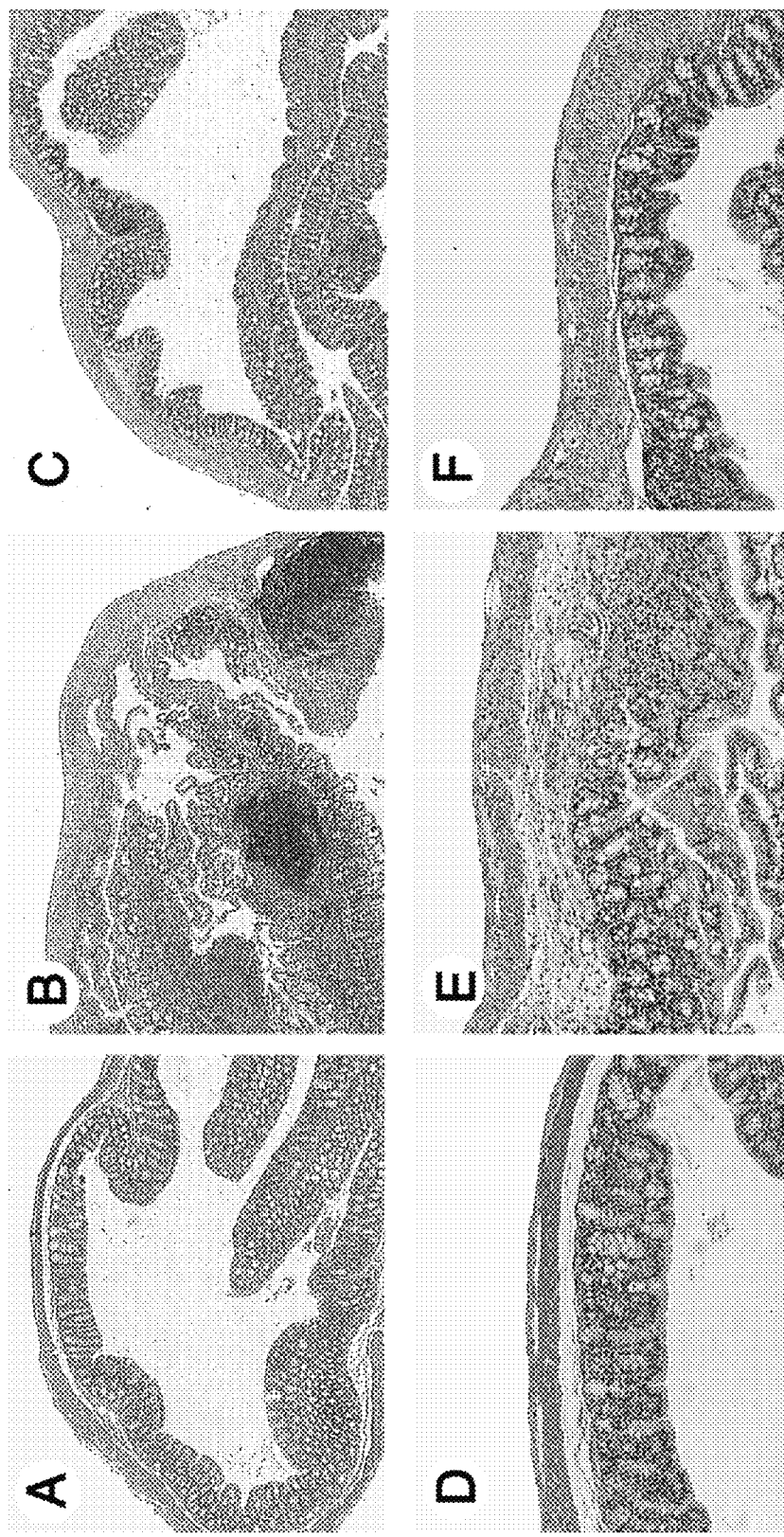
FIG. 2A is a photomicrograph of hematoxylin and eosin (H&E)-stained paraffin-embedded colonic tissue recovered from mice fed the punicic acid during Experiment 1 at 20× magnification.
FIG. 2B is a photomicrograph of H&E-stained paraffin-embedded colonic tissue recovered from mice fed the punicic acid diet during Experiment 1 at 20× magnification.
FIG. 2C is a photomicrograph of H&E-stained paraffin-embedded colonic tissue recovered from mice fed the control diet during Experiment 1.
FIG. 2D is a photomicrograph of H&E-stained paraffin-embedded colonic tissue recovered from mice fed the control diet during Experiment 1.
FIG. 2E is a photomicrograph of H&E-stained paraffin-embedded colonic tissue recovered from mice fed the punicic acid diet during Experiment 1 at 40× magnification.
FIG. 2F is a photomicrograph of H&E-stained paraffin-embedded colonic tissue recovered from mice fed the punicic acid diet during Experiment 1 at 40× magnification.

Specifically, following the DSS challenge, the average macroscopic score (on a scale from 0 to 3) in colons of mice fed the control diet was 3 whereas in punicic acid-fed mice the score was 1.4. The average colon weights in control-fed mice were 0.958 grams whereas those of punicic acid-fed mice averaged 0.153 grams. These lower colon weights and milder lesions can be caused by decreased inflammatory cell migration into the colon. Histopathological examination of the H&E-stained slides of colon under the microscope revealed no major lesions in punicic acid fed mice, whereas mice fed the control diet presented thickening of the colonic mucosa, epithelial erosion, and infiltration of inflammatory cells. At 20×, a loss of the epithelial surface was observed in FIG. 2C when compared with FIG. 2A. At a magnification of 40×, FIGS. 2E and 2F showed inflammatory cell infiltration, flattening of epithelial cells and epithelial erosion. FIG. 2B showed a thickening of the colonic mucosa without erosion or infiltration. FIG. 2D showed the epithelial cells maintained their normal columnar shape.

The scoring of the pathological findings reveals that the severity of colonic lesions in control-fed mice was greater than in punicic acid-fed mice (Table 1).

TABLE 1

Histological scores following a 7-day challenge period with 2.5% DSS.

| Item | Control Diet | PUNICIC ACID diet | P value |
|---|---|---|---|
| Mucosal Thickness | 4.00 ± 0.42* | 1.83 ± 0.24 | 0.0146 |
| Epithelial Erosion | 4.00 ± 0.12* | 0.00 ± 0.00 | 0.0001 |
| Inflammatory Cell Infiltration | 4.00 ± 0.30* | 0.50 ± 0.17 | 0.0001 |
| Vascular Changes | 0.50 ± 0.20 | 0.50 ± 0.35 | 0.1927 |
| Metaplasia/ Hyperplasia | 3.50 ± 0.50* | 0.50 ± 0.28 | 0.0061 |
| Crypt Damage | 4.00 ± 0.45 | 0.33 ± 0.26 | 0.0009 |

Values are least square means ± standard error of the mean.
*Illustrates that the value is statistically different.

It is generally accepted that the goals of IBD preventive or therapeutic approaches include inducing substantial clinical improvements (Lichtenstein et al. 2003). The oral administration of punicic acid resulted in significant clinical and pathological improvements. In addition, the macroscopic and histologic (data not shown) analysis of key organs involved in metabolism (i.e., liver and kidneys) and the brain revealed no abnormalities, which suggests that the dose utilized was effective and safe. No adverse effects were observed throughout the duration of the study.

Experiment 2

Objective

To examine the effect of punicic acid on immune system development, lymphocyte numbers and lymphocyte function.

Methods

Administration, dosage, and punicic acid preparation were the same as in Experiment 1.

Media and Reagent Preparation

After preparation of each media or buffer, the final product was labeled with the following: 1) Name of the product, 2) Preparation date, 3) Expiration date, 4) Storage recommendations, 5) Technician's initials, and 6) Sterility status. The first media prepared was cRPMI. The formulation is based on a series of cellular media utilizing a bicarbonate buffering system and alterations in the amounts of amino acids and vitamins. cRPMI media has been used for the culture of normal human and neoplastic leukocytes. When properly supplemented, cRPMI has wide applicability for supporting growth of many types of cultured cells, including fresh human lymphocytes. cRPMI was prepared in the following manner:

| cRPMI: | |
|---|---|
| Amount | Component |
| 400 mL | RPMI 1640 |
| 50 mL | Fetal Calf Serum |
| 5 mL | Sodium Pyruvate |
| 5 mL | Non-Essential Amino Acids |
| 10 mL | Essential Amino Acids |
| 5 mL | L-Glutamine |
| 5 mL | Penicillin-Streptomycin |
| 12.5 mL | 1M Hepes Buffer |

The composition of cRPMI is well known in the art (Bassaganya-Riera et al. 2001). All components are combined under a sterile laminar flow hood (Nuaire, Plymouth, Minn.), and sterilized by filtration using a 0.22-micron membrane filter with a 60-micron pre-filter (Fisher, Atlanta, Ga.). The prepared media is prepared in an etoxaclean-cleaned (Sigma, Saint Louis, Mo.), autoclaved, sterile, screw-cap, glass, 500-mL bottle (30 minutes at 121° C. at 15 PSI), labeled and stored at 4° C.

FACS and PBS buffers were prepared according to the following concentrations.

| Amount | Component |
|---|---|
| FACS buffer: | |
| 500 mL | 1X PBS |
| 5 mL | Fetal Calf Serum |
| 1 mL | 10% Sodium Azide |

After combining the ingredients, the FACS buffer is labeled and stored at 4° C.

| PBS (1X): | |
|---|---|
| 1,000.00 mL | Deionized Water* |
| 8.00 g | Sodium Chloride |
| 1.15 g | Sodium Phosphate |
| 0.20 g | Potassium Chloride |
| 0.20 g | Potassium Phosphate |

| PBS (10X): | |
|---|---|
| 1,000.00 mL | Water |
| 80.00 g | Sodium Chloride |
| 11.50 g | Sodium Phosphate |
| 2.00 g | Potassium Chloride |
| 2.00 g | Potassium Phosphate |

*Deionized water was obtained from an E-Pure water purification system (Barnstead Int., Dubuque, IA).

After combining the ingredients and stifling for 30 minutes, the solution was autoclaved (Brinkman, Tuttnauer, Jerusalem, Israel) for 30 minutes at 121° C. at 15 PSI. The pH was adjusted to 7.2 (AR15 PH/MV/TEMP meter, Accumet, Arvada, Co.) by adding either concentrated hydrochloric acid or sodium bicarbonate.

A total of twenty-two C57BL6 mice were used in Experiment 2. All mice were born on Nov. 23, 2003, weaned on Dec. 16, 2003 and fed the experimental diets from Dec. 19, 2003 to Jan, 15, 2004. A total of 10 mice were fed a control diet and 12 mice were fed a diet supplemented with punicic acid (0.6 g punicic acid/100 g food). Mice were weighed on a weekly basis. Mice were euthanized. Blood was collected from each mouse for generating serum, which was stored at −20° C. Thymus, spleen and colonic lymph nodes were harvested, weighed and collected in cRPMI in sterile conditions. Colon and liver specimens were collected in RNA later (Ambion Inc., Austin, Tex.) and frozen at −80° C. for gene expression analysis. Brain, kidney, liver, colon and ileum were also collected in a 10% buffered neutral formalin solution and processed as described in experiment 1 for histological evaluation. The remaining portion of the carcass was stored in 50-mL, conical tubes and frozen at −20° C. for body composition and fatty acid analysis. All specimens were generally labeled with the following information: 1) mouse number; 2) date collected; 3) experiment number; 4) type of solvent; and 5) tissue type. Tissue slides were examined in an Olympus microscope (Olympus America Inc., Dulles, Va.). Images were captured using the FlashBus FBG software (Integral Technologies, Indianapolis, Ind.) and processed in Adobe Photoshop Elements 2.0 (Adobe Systems Inc., San Jose, Calif.).

Spleens, thymuses and colonic lymph nodes were collected in complete RPMI on ice. Single-cell suspensions were obtained from each tissue by gently disrupting the tissue between two frosted ends of two glass slides on a petri dish containing 3 mL of cRPMI. The single-cell suspension was transferred from the petri dish to a 15-mL polypropylene tube (Fisher, Atlanta, Ga.) and washed by centrifuging in an Eppendorf 5810 R centrifuge (Westbury, N.Y.) at 200×g for 5 minutes at 4° C. The supernatant was discarded by decantation of the tube. The cell pellet was broken by gently tapping the tube against a solid surface. The total numbers of spleenocytes, thymocytes and colonic lymph node lymphocytes in each mouse were enumerated in a Z1 Coulter Single Particle Counter (Miami, Fla.). Briefly, 10 mL of isoton II diluent solution (Beckman Coulter, Miami, Fla.) were added into a counting vial, followed by 40 μL of the cell suspension, 4 drops of Zapaglobin (Beckman Coulter, Miami Fla.), and 10 additional mL of the isoton solution. The volume in which the cells were resuspended was assessed using a 5-mL, sterile pipette. The concentration of cells/mL and the total volume in each tube were used to determine the total amount of cells in each tissue and mouse.

Flow Cytometry

Flow cytometry provides an efficient, sensitive and quantitative method of analyzing the phenotype of cells, including lymphocytes. Cells express proteins on the surface membrane that can be used to include them in specific populations or subpopulations and infer certain functional characteristics such as an ability to proliferate and an ability to produce antibodies etc. Monoclonal antibodies (mAbs) bind these proteins (e.g., CD4, CD3, CD8, alphabeta-TCR, gammadelta-TCR, and CD19) in a species-specific manner. For flow cytometric applications, mAbs are labeled with different fluorescent dyes (e.g., phycoerythrin, PE; fluorescein isothiocyanate, FITC, cychrome, Cy). Flow cytometry is currently being utilized both in research (e.g., immunophenotyping, measuring lymphocyte activation etc.) and in the diagnoses of human immunodeficiency virus-induced lymphoid depletion, leukemia and lymphoma, and monitoring of transplant rejection.

To evaluate the effects of punicic acid on $CD4^+$, $CD8^+$ T-cell receptor (TCR)alphabeta$^+$, TCRgammadelta$^+$, and $CD19^+$ lymphocytes in spleen, thymus and colonic lymph nodes, the phenotypes of splenocytes, thymocytes and colonic lymph node lymphocytes recovered from punicic acid-fed and control diet-fed mice were examined by flow cytometry. A description of the uses of flow cytometry was provided in Experiment 1. Splenocyte suspensions were freed of erythrocytes by osmotic lysis (adding 4.5 mL of sterile deionized water for 1 to 2 seconds and then adding 0.5 mL of 10×PBS to make 1×PBS solution). Cells were washed again by centrifuging in an Eppendorf 5810 R centrifuge (Westbury, N.Y.) at 200×g for 5 minutes at 4° C. The supernatant was discarded by decantation of the tube. The cell pellet was broken by gently tapping the tube against a solid surface. FACS buffer (1 mL) was added in each tube. Splenocytes, thymocytes and colonic lymph node-derived mononuclear cells were enumerated in a Z1 Coulter Single Particle Counter (Miami, Fla.), adjusted to $2\times10^6$ cells/mL. Splenocytes, thymocytes, and colonic lymph nodes were analyzed for expression of CD4, CD8, CD3, TCRalphabeta, TCRgammadelta and CD 19 molecules by flow cytometry as previously described (Bassaganya-Riera et al. 2001; Bassaganya-Riera et al. 2002; Bassaganya-Riera et al. 2003). Briefly, a volume of 100 μl of the splenocyte, thymocyte, and colonic lymph node lymphocyte suspension was added in to a round-bottomed microtiter plate (Becton Dickinson, Lincoln Park, N.J.) and stained with 50 μl of the primary antibody solutions in FACS buffer. Anti-mouse CD8-PE (1:200 dilution); anti-mouse CD4-FITC, (1:500 dilution); anti-mouse CD3-Cy-Chrome (1:500 dilution); anti-mouse alphabeta-TCR-PE (1:200 dilution), anti-mouse gammadelta-TCR-FITC (1:500 dilution); and anti-mouse CD19-PE (1:500 dilution). Expression of CD4 and CD8 was examined in a two-color analysis, whereas expression of CD19 was examined in a single-color analysis. Data acquisition was performed using a Coulter EPIC XL-MCL flow cytometer (Miami, Fla.). Data analyses were performed using the CellQuest software (BD Biosciences, San Diego, Calif.).

Lymphocyte Blastogenesis Test cRPMI medium was prepared as shown above. Wells of 96-well flat-bottomed microtiter plates (Becton Dickinson, Lincoln Park, N.J.) were seeded with $2\times10^5$ mononuclear cells in a total volume of 200 μl per well. Wells contained either concanavalin A (5 ConA; Sigma), or medium alone (non-stimulated). Plates were incubated for 5 days at 37° C. in 5% $CO_2$ humidified atmosphere. After 5 days, 0.5 ∞Ci of methyl-[$^3$H] thymidine (specific radioactivity 6.7 Ci mmol$^{-1}$; Amersham Life Science, Arlington Heights, Ill.) in 10 μl of medium was added to each well and plates incubated for an additional 20 h. Well contents were harvested onto fiber filters with a PHD cell harvester (Skatron Instruments Inc., Sterling, Va.) and incorporated radioactivity measured by liquid scintillation counting (Beckman Instruments, Schaumburg, Ill.). Samples were run in triplicate and stimulation indices (SI) calculated by dividing counts min$^{-1}$ of stimulated wells by counts min$^{-1}$ from non-stimulated wells. The lymphocyte blastogenesis assay was performed as previously described by the inventor (Bassaganya-Riera et al. 2001; Bassaganya-Riera et al. 2002; Bassaganya-Riera et al. 2003).

Statistical analysis was performed by analysis of variance (ANOVA). The ANOVA was performed using the general linear model procedure of SAS (SAS 1988) as previously described (Bassaganya-Riera et al. 2003). Differences with a probability value (P<0.05) were considered statistically significant.

Results

The lymph nodes are secondary lymphoid organs where immune responses against viruses and bacteria or other foreign antigens are initiated. With the exception of gammadelta T cells, naïve lymphocytes recirculate from the blood to the lymph nodes and from lymph nodes into tissues. More densely populated lymph nodes are likely to contribute to initiating stronger and more effective immune responses against foreign antigens. The results demonstrate that the total number of lymphocytes in the lymph nodes of punicic acid-fed mice is greater (P<0.0043) than that of lymph nodes from control-fed mice. While the weight of the lymph node was also numerically greater in punicic acid-fed mice (223.33 versus 261.66 mg), it was not statistically significant. In addition, the phenotypic analysis of the lymphocyte subpopulations of the lymph nodes reveals that the lymphocyte subpopulations, which were significantly expanded, included $CD4^+$ T cells, $CD8^+$ T cells and TCR alphabeta $(\alpha\beta)^+$ T cells. The numbers of B cells in punicic acid-fed mice were not significantly greater than those of mice fed the control diet. This data suggests that punicic acid-fed mammals, including humans, are able to induce more effective T cell responses than those not fed punicic acid. This finding has likely implications on modulating the immune system development, general immune health and infectious disease resistance. Table 2 depicts the differences between lymph nodes recovered from mice fed punicic acid or a control diet.

TABLE 2

Phenotypic and developmental analysis of colonic lymph nodes.

| Item | Control Diet | Punicic Acid Diet | P value |
|---|---|---|---|
| Weight (mg) | 223.33 ± 3.79 | 261.66 ± 3.28 | 0.4544 |
| Lymphocytes ($\times10^6$/mL) | 11.03 ± 1.77 | 18.64 ± 1.53* | 0.0043 |
| $CD8^+$ T cells | 2.69 ± 0.46 | 4.53 ± 0.41* | 0.0083 |
| $CD4^+$ T cells | 4.10 ± 0.64 | 6.65 ± 0.58* | 0.0087 |
| $CD3^+$ T cells | 6.07 ± 0.94 | 10.24 ± 0.85* | 0.0043 |
| $CD19^+$ T cells | 3.80 ± 0.80 | 5.98 ± 0.72* | 0.0602 |
| TCR $\alpha\beta^+$ T cells | 6.59 ± 1.14 | 11.78 ± 1.08* | 0.0042 |

Values are least square means ± standard error of the mean.
*Illustrates that the value is statistically different.

The spleen is another crucial organ of the immune system. The events occurring in the spleen are representative of changes occurring in recirculating lymphocytes in blood. The weight of the spleens in punicic acid-fed mice was significantly greater than that of control fed mice (P<0.0151). The spleen was larger due to greater numbers of $\alpha\beta^+$ T cells (P<0.0352). This population of lymphocytes includes $CD4^+$ and $CD8^+$ T cells. (Table 3).

TABLE 3

Phenotypic and developmental analysis of the spleen.

| Item | Control Diet | Punicic Acid diet | P value |
|---|---|---|---|
| Weight (mg) | 752.22 ± 3.65 | 884.54 ± 3.30* | 0.0151 |
| Total # of lymphocytes (×10$^6$/mL) | 148.87 ± 7.89 | 144.21 ± 7.13 | 0.6662 |
| CD8$^+$ T cells | 13.19 ± 0.80 | 12.72 ± 0.73 | 0.6737 |
| CD4$^+$ T cells | 16.08 ± 1.22 | 17.04 ± 1.10 | 0.5697 |
| CD3$^+$ T cells | 29.25 ± 1.97 | 30.05 ± 1.78 | 0.7675 |
| CD19$^+$ T cells | 106.59 ± 4.99 | 102.22 ± 5.42 | 0.5960 |
| TCR αβ$^+$ T cells | 29.37 ± 2.13 | 33.12 ± 1.93* | 0.0352 |

Values are least square means ± standard error of the mean.
*Illustrates that the value is statistically different.

The thymus is the main organ of the immune system where T cell precursors originated in the bone marrow mature and differentiate into mature T cells, which can be released into the bloodstream and repopulate secondary lymphoid organs such as spleen and lymph nodes. The significantly greater weight of the thymus in punicic acid-fed mice indicates that punicic acid favors thymocyte development. The main population that contributed to this greater thymus size and cellularity was the CD4$^+$CD8$^+$ double-positive thymocytes. These thymocytes represent the maturation step before the generation of mature CD4$^+$ or CD8$^+$ T cells. Some of the double-positive lymphocytes will differentiate into CD4$^+$ T cells and others into CD8$^+$ T cells. These data demonstrate that punicic acid contributes to thymic development and thus to immune system development (Table 4).

TABLE 4

Phenotypic and developmental analysis of the thymus.

| Item | Control Diet | Punicic Acid Diet | P value |
|---|---|---|---|
| Weight (mg) | 611.11 ± 5.41 | 845.00 ± 4.68* | 0.0041 |
| Lymphocytes (×10$^6$/mL) | 63.09 ± 11.04 | 69.18 ± 9.56 | 0.6814 |
| CD8$^+$ thymocytes | 1.36 ± 0.21 | 1.34 ± 0.18 | 0.9447 |
| CD4$^+$CD8$^+$ thymocytes | 56.48 ± 10.09 | 63.25 ± 8.73 | 0.6178 |
| CD4$^+$ thymocytes | 2.39 ± 0.33 | 2.51 ± 0.28 | 0.7885 |
| TCR αβ$^+$ thymocytes | 7.39 ± 1.40 | 9.12 ± 1.21 | 0.3617 |

Values are least square means ± standard error of the mean.
*Illustrates that the value is statistically different.

Tables 1-4 show that punicic acid enhances the development of the immune system (i.e., immune organ weight and/or cellularity) and increases the numbers of T cells (i.e., CD4$^+$ and CD8$^+$) in a mammal. Table 5 examines whether punicic acid modulates the functional ability of these lymphocytes. Specifically, Table 5 illustrates the proliferative ability of lymphocytes in response to stimulation with the T cell mitogen Con A. The results show that the proliferative ability of splenocytes recovered from punicic acid-fed mice is significantly greater than those recovered from mice fed the control diet. A possible application of this finding is that T cells from PUA-fed mice will be able to multiply more rapidly and respond against pathogens during an infection. The same numerical trend can be observed when comparing the proliferative abilities of lymph node-derived lymphocytes. However, these numerical differences in the lymph nodes were not statistically significant.

TABLE 5

Proliferation of lymphocytes in response to stimulation with Con A.

| Item | Control Diet | Punicic Acid Diet | P value |
|---|---|---|---|
| Counts/minute spleen (cRPMI) | 58.66 ± 12.66 | 73.17 ± 10.96 | 0.3974 |
| Counts/minute spleen (cRPMI & ConA) | 694.00 ± 293.78 | 1905.27 ± 254.42* | 0.0057 |
| Stimulation index spleen | 14.25 ± 3.65 | 25.20 ± 3.16* | 0.0354 |
| Counts/minute lymph nodes (cRPMI) | 35.05 ± 4.35 | 43.12 ± 3.76 | 0.1772 |
| Counts/minute lymph nodes (cRPMI & ConA) | 516.51 ± 186.03 | 929.06 ± 161.10 | 0.1100 |
| Stimulation index lymph nodes | 14.83 ± 4.16 | 22.40 ± 3.61 | 0.1856 |

Values are least square means ± standard error of the mean.
*Illustrates that the value is statistically different.

Experiment 3

Objective

To determine the effect of punicic acid on cellular immune responses against influenza virus antigens following vaccination.

Methods

A total of twenty-five C57BL6 mice were used in Experiment 3. Ten mice were fed a control diet and 15 mice were fed a diet supplemented with punicic acid (0.6 g punicic acid/100 g food). All mice were fed either the control or punicic acid-supplemented diets for 9 weeks prior to the immunization with an influenza virus (VR-1469) vaccine consisting of 100 μg of UV-inactivated influenza virus antigens in Freunds Incomplete adjuvant. Mice were killed on week 15 of dietary supplementation. Spleens were collected in sterile, cRPMI on ice. Single-cell suspensions were obtained from each tissue as described in Experiment 1. The single-cell suspension was transferred from the petri dish to a 15-mL polypropylene tube (Fisher, Atlanta, Ga.) and washed by centrifuging in an Eppendorf 5810 R centrifuge (Westbury, N.Y.) at 200×g for 5 minutes at 4° C. The supernatant was discarded by decantation of the tube. The cell pellet was broken by gently tapping the tube against a solid surface. Splenocytes were enumerated in a Z1 Coulter Single Particle Counter (Miami, Fla.). Briefly, 10 mL of isoton II diluent solution (Beckman Coulter, Miami, Fla.) were added into a counting vial, followed by 40 μL of the cell suspension, 4 drops of Zap-oglobin (Beckman Coulter, Miami Fla.), and 10 additional mL of the isoton solution and utilized in functional assays.

Carboxy Fluoroscein Succinimidyl Ester (CFSE) Proliferation Assay

A total of 2×10$^7$ splenocytes were separated to perform CFSE proliferation assay (Molecular Probes). Cells were centrifuged (200×g) for 5 min and supernatants aspirated. While cells were in the centrifuge 1 stock vial of CFSE was diluted to 10 mM (Component A) in 90 μL of dimethyl sulfoxide (Component B). The 10 mM CFSE solution was diluted to 1 μM. A total of 2×10$^7$ splenocyte pellets were resuspended in 1 mL of the 5 μM CFSE solution, incubated for 10 minutes in the dark at 37° C. in a 5% CO$_2$ humidified atmosphere. Cells were re-pelleted and resuspended in 3 mL of RPMI-1640 containing 10% fetal calf serum and pre-warmed at 37° C. Cells were then incubated for 15 additional minutes in the dark at 37° C. in a 5% CO$_2$ humidified atmosphere. A volume of 3 mL of RPMI-1640 containing 10% fetal calf serum was added and the cell suspension was centrifuged (200×g) for 5 min and supernatants aspirated by using a sterile Pasteur pipette. The last two steps were repeated once more and cells were then resuspended in cRPMI. CFSE-stained splenocytes were enumerated and the cell concentration was adjusted to $2 \times 10^6$ splenocytes/mL of cRPMI. Cell suspensions (100 µl) were added to 96-well flat-bottomed microtiter plates containing 100 µl of medium (non-stimulated), or medium plus 10 µg/ml of VR-1469 influenza virus antigens. Samples were run in replicates of six for each animal and ex-vivo treatment. Cells were incubated at 37° C. in 5% $CO_2$ humidified atmosphere for 5 days. As cells divide, CFSE membrane staining diminishes resulting in a decreased mean fluorescence intensity. This characteristic is utilized to distinguish between proliferating and non-proliferating lymphocytes based on mean fluorescence intensity. After a 6 day period, cultured cells from the six wells of the same ex vivo treatment and mouse were pooled and prepared for immunophenotyping. A volume of 100 µl of CFSE-stained spleenocytes was added in to a round-bottomed microtiter plate (Becton Dickinson, Lincoln Park, N.J.) and stained with 50 µl of the primary antibody solutions in FACS buffer: Anti-mouse CD8-PE (1:200 dilution); anti-mouse CD4-Biotin (1:500 dilution); anti-mouse CD3-CyChrome (1:500 dilution); anti-mouse beta-TCR-PE (1:200 dilution); anti-mouse gammadelta-TCR-FITC (1:500 dilution); and anti-mouse CD19-PE (1:500 dilution). The staining of the CD4 versus CD8 required an extra step of adding streptavidin-Cychrome, which binds to the biotin. Cell surface phenotype was examined in a three-color analysis. Data acquisition was performed using a Coulter EPIC XL-MCL flow cytometer (Miami, Fla.).

Results

While the results of Experiment 2 indicate dietary punicic acid-supplementation enhances the ability of lymphocytes to proliferate (multiply) in response to a general mitogenic stimulus (a stimulus that induces proliferation), the results of Experiment 3 show punicic acid also enhances the ability of lymphocytes to respond against viruses following vaccination with influenza virus (flu virus). Experiment 3 examined the ability of punicic acid to regulate immune responses against influenza virus antigens and characterized one of the cellular targets (i.e., $CD8^+$ T cells) of punicic acid's actions. By examining the influenza virus-specific proliferation of lymphocyte subsets we found that punicic acid enhanced the proliferative ability of $CD8^+$ T cells in response to influenza virus (Table 6). This finding is consistent with the previous results reported in Experiment 2 and has implications on viral disease resistance and prevention of the common cold and flu in vaccinated animals.

Experiment 3 also represented a long-term dietary supplementation study (105 days). Throughout the study, mice were monitored for adverse effects or clinical signs. No negative adverse effects associated with dietary punicic acid-supplementation were observed throughout the study. At the end of the study the brain, kidneys, liver, heart and lungs were collected and fixed in formalin for histological analyses. H&E stained slides revealed no microscopic lesions in any of these organs. Hence, punicic acid modulated immune function effectively but was also safe during the course of a 105-day supplementation period.

Experiment 4

Objective

To determine the effect of punicic acid on the development of obesity and Type 2 diabetes induced by high fat diets. Specifically, we investigated whether punicic acid was able to normalize impaired glucose tolerance, prevent hyperglycemia and hyperinsulinemia and attenuate abdominal fat accumulation in mice fed high fat diets.

Methods

In Western countries, Metabolic Syndrome or Syndrome X (i.e., diabetes, obesity, cardiovascular disease, hypertension and hyperlipidemia) is on a steady rise. The development of nutrition-based therapeutic or preventive interventions using orally active, natural compounds is not only timely but also urgently needed. A total of fifty C57BL6 mice were used in experiment 4. Twenty-five mice were fed a control diet and twenty-five mice were fed a diet supplemented with punicic acid (0.6 g punicic acid/100 g food). For the first 32 days of the experiment all diets contained 7% fat, 0.02 total cholesterol and they obtained 14.5% of calories from fat by replacing punicic acid with linoleic acid (wt/wt basis) in the control diet (Table 7). These diets are defined as regular diets and were formulated to be isocaloric between treatment groups. On day 32 of the experiment, twenty mice within each group were fed high fat diets containing 19.6% fat, 0.2% total cholesterol that obtained 40.1% of calories from fat by replacing punicic acid with lard (wt/wt basis) in the control high fat diet (Table 8). The high fat diets were also formulated to be isocaloric between treatment groups. The remaining mice within each group (n=5) were fed the regular diets. On day 78 of the experiment, mice were killed, blood was collected and immediately analyzed for fasting glucose concentrations by using the Accu-Check Instant Plus System (Roche Diagnostics Corporation, Indianapolis, Ind.) or stored for subsequent analysis of insulin concentrations in plasma. Abdominal white adipose tissue and interscapular brown adipose tissue

TABLE 6

Subset-specific Proliferation of Lymphocytes in Response to Stimulation with Influenza Virus antigens.

| | Unvaccinated | | Vaccinated | | |
|---|---|---|---|---|---|
| Item | Control | Punicic Acid | Control | Punicic Acid | P value |
| Relative Proliferation Index $CD8^+$ T cells | 0.78 ± 0.18 | 0.57 ± 0.36 | 0.60 ± 0.40 | 1.15 ± 0.37* | 0.06 |
| Relative Proliferation Index $CD4^+$ T cells | 0.88 ± 0.31 | 0.68 ± 0.48 | 0.76 ± 0.58 | 1.10 ± 0.63 | 0.33 |
| Relative Proliferation Index B cells | 1.00 ± 0.04 | 1.15 ± 0.63 | 0.96 ± 0.57 | 1.16 ± 0.27 | 0.90 |

Values are least square means ± standard error of the mean.
*Illustrates that the value is statistically different.

were collected, weighed and stored at −80° C. for RNA analyses. Liver, lungs, kidneys, pancreas and heart were examined for macroscopic abnormalities (gross lesions), fixed in phosphate-buffered formalin (10%) and processed as described in experiment 1 for histological evaluation. All specimens were generally labeled with the following information: 1) mouse number; 2) date collected; 3) experiment number; 4) type of solvent; and 5) tissue type.

TABLE 7

Composition of the Regular Diets[1].

| Ingredient | Control Diet | PUA Diet |
|---|---|---|
| Casein | 200 | 200 |
| L-Cystine | 3 | 3 |
| Corn Starch | 397.486 | 397.486 |
| Maltodextrin | 132 | 132 |
| Sucrose | 100 | 100 |
| Cellulose | 50 | 50 |
| Mineral Mix (AIN-93)[2] | 35 | 35 |
| Vitamin Mix (AIN-93)[3] | 10 | 10 |
| Choline Bitartrate | 2.5 | 2.5 |
| tert-butylhydroquinone[4] | 0.014 | 0.014 |
| Soybean oil | 60 | 60 |
| Linoleic acid | 10 | — |
| Pomegranate oil | — | 10 |

[1]Provides approximately 7% fat and 0.02 total cholesterol and it obtains 14.5% of calories from fat.
[2]Supplied per kg of diet: 3 g nicotinic acid, 1.6 g calcium pantotenate, 0.7 g pyridoxine HCl, 0.6 g Thiamin HCl, 0.6 g riboflavin, 0.2 g folic acid, 0.02 g D-biotin, 2.5 g vitamin $B_{12}$ (0.1% in mannitol), 15 g DL-alpha tocopheryl acetate (500 IU/g), 0.8 g vitamin A palmitate (500,000 IU/g), 0.2 g vitamin $D_3$ (cholecalciferol, 500,000 IU/g), 0.075 g vitamin K (phylloquinone), and 974.705 g sucrose.
[3]Supplied per kg of diet: 357 g calcium carbonate, 196 g potassium phosphate monobasic, 70.78 g potassium citrate, 74 g sodium chloride, 46.6 g potassium sulfate, 24.3 g magnesium oxide, 6.06 g ferric citrate, 1.65 g zinc carbonate, 0.63 g manganous carbonate, 0.31 g cupric carbonate, 0.01 g potassium iodate, 0.01025 g sodium selenate, 0.00795 g ammonium paramolybdate, 1.45 g sodium meta-silicate, 0.275 g chromium potassium sulfate, 0.0174 g lithium chloride, 0.0815 g boric acid, 0.0635 g sodium fluoride, 0.0318 g nickel carbonate, hydroxide, tetrahydrate, 0.0066 g ammonium vanadate, and 220.716 g sucrose.
[4]Antioxidant.

TABLE 8

Composition of the High Fat Diets[1].

| Ingredient | Control Diet | PUA Diet |
|---|---|---|
| Casein | 232 | 232 |
| L-Cystine | 3.0 | 3.0 |
| DL-Methionine | 3.5 | 3.5 |
| Corn Starch | 137 | 137 |
| Maltodextrin | 150 | 150 |
| Sucrose | 162.595 | 162.595 |
| Cellulose | 50 | 50 |
| Cholesterol | 1.9 | 1.9 |
| Mineral Mix (AIN-93)[2] | 40.60 | 40.60 |
| Calcium phosphate dibasic | 4.64 | 4.64 |
| Vitamin Mix (AIN-93)[3] | 16.24 | 16.24 |
| Choline Bitartrate | 5 | 5 |
| tert-butylhydroquinone[4] | 0.02 | 0.02 |
| Vitamin K, phylloquinone | 0.005 | 0.005 |
| Soybean oil | 30 | 30 |
| Lard | 163.5 | 153.5 |
| Pomegranate oil | — | 10 |

[1]Provides approximately 19.6% fat and 0.2% total cholesterol and it obtains 40.1% of calories from fat.
[2]Supplied per kg of diet: 3 g nicotinic acid, 1.6 g calcium pantotenate, 0.7 g pyridoxine HCl, 0.6 g Thiamin HCl, 0.6 g riboflavin, 0.2 g folic acid, 0.02 g D-biotin, 2.5 g vitamin $B_{12}$ (0.1% in mannitol), 15 g DL-alpha tocopheryl acetate (500 IU/g), 0.8 g vitamin A palmitate (500,000 IU/g), 0.2 g vitamin $D_3$ (cholecalciferol, 500,000 IU/g), 0.075 g vitamin K (phylloquinone), and 974.705 g sucrose.
[3]Supplied per kg of diet: 357 g calcium carbonate, 196 g potassium phosphate monobasic, 70.78 g potassium citrate, 74 g sodium chloride, 46.6 g potassium sulfate, 24.3 g magnesium oxide, 6.06 g ferric citrate, 1.65 g zinc carbonate, 0.63 g manganous carbonate, 0.31 g cupric carbonate, 0.01 g potassium iodate, 0.01025 g sodium selenate, 0.00795 g ammonium paramolybdate, 1.45 g sodium meta-silicate, 0.275 g chromium potassium sulfate, 0.0174 g lithium chloride, 0.0815 g boric acid, 0.0635 g sodium fluoride, 0.0318 g nickel carbonate, hydroxide, tetrahydrate, 0.0066 g ammonium vanadate, and 220.716 g sucrose.
[4]Antioxidant.

Glucose Tolerance Tests

A glucose tolerance test was conducted on day 78 of the experiment. Animals were fasted overnight (14 hours). Mice were injected intraperitoneally with D-glucose (1 mg/kg body weight) and blood samples were collected via the tail vein prior to the injection (time 0) and at 15, 30 and 60 minutes following the injection.

Determination of Serum Insulin Concentrations

Serum insulin concentrations were determined by using commercially available enzyme-linked immunosorbent assay kits (Linco Research, St. Charles, Mo.).

Statistics

Data were analyzed by analysis of variance (ANOVA). The ANOVA was performed by using the general linear model procedure of SAS (SAS Institute Inc., Cary, N.C.) as previously described (Bassaganya-Riera et al. 2004). Differences with probability value (P<0.05) were considered significant.

Results

Figure 3A:
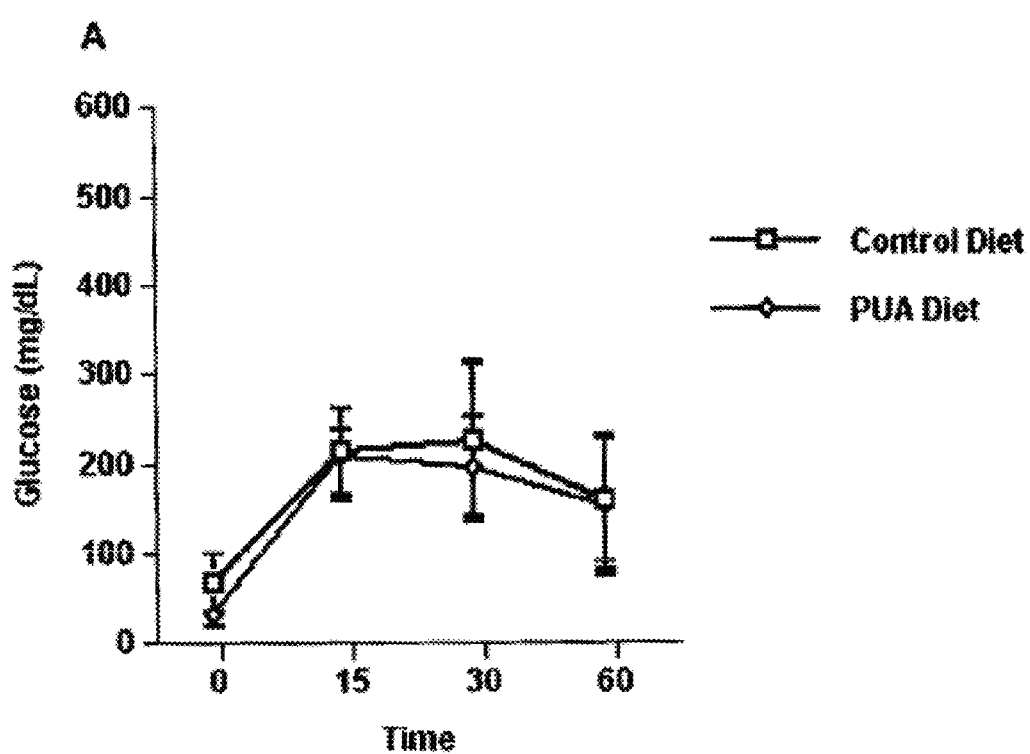
FIG. 3A is a graph illustrating the effect of punicic acid on blood glucose concentrations in mice fed regular diets from Experiment 4.
Figure 3B:
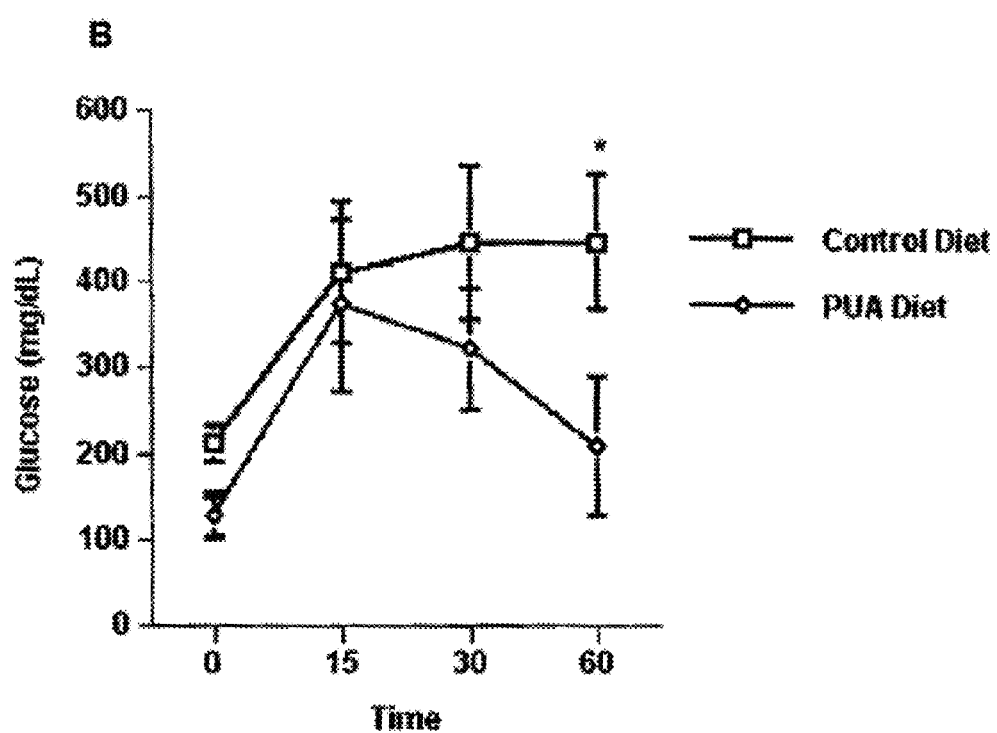
FIG. 3B is a graph illustrating the effect of punicic acid on blood glucose concentrations in mice fed high fat diets from Experiment 4.

Excessive abdominal fat accumulation and insulin resistance are key characteristics that typify the Metabolic Syndrome. The glucose tolerance tests are standard methods for evaluating glucose homeostasis in vivo. By using the glucose tolerance test, we discovered that glucose tolerance was not different between the two groups fed regular diets, which did not develop a diabetic phenotype (FIG. 3A). However, the ability of mice fed a control high fat diet to normalize impaired glucose tolerance was significantly impaired when compared to those fed the high fat diets supplemented with punicic acid (FIG. 3B).

TABLE 9

Weight of abdominal white adipose tissue and interscapular brown adipose tissue and plasma fasting glucose and insulin concentrations in mice fed control or punicic acid (PUA)-supplemented regular and high fat diets[1].

| | Regular Diets | | High Fat Diets | | | ANOVA |
|---|---|---|---|---|---|---|
| Item | Control | PUA | Control | PUA | SEM[2] | P value |
| White adipose tissue, g | 0.865[b] | 0.801[b] | 1.478[a] | 0.830[b] | 0.06 | 0.0001 |
| Brown adipose tissue, g | 0.130 | 0.138 | 0.129 | 0.124 | 0.008 | 0.08 |
| Glucose (mg/dL) | 153.8[b] | 121.40[b] | 301.30[a] | 219.5[b] | 11.3 | 0.0001 |
| Insulin (ng/mL) | 0.932[b] | 0.669[b] | 2.254[a] | 1.229[b] | 0.23 | 0.01 |

[1]Least squares means values in a row for a particular tissue with different superscripts are significantly different (P < 0.05).
[2]Pooled standard error of the least square means.

Furthermore, mice fed the control high fat diet were markedly more hyperglycemic and hyperinsulinemic than mice fed high fat diets supplemented with punicic acid or mice fed regular diets (Table 9). Thus, punicic acid-supplementation prevents or ameliorates the development of hyperglycemia, attenuates the hyperinsulinemia and normalizes impaired glucose tolerance in mice fed high fat diets (Table 9). These findings are clinically significant in the prevention and treatment of Type 2 diabetes, the Metabolic Syndrome and their complications (e.g., cardiovascular disease, stroke, retinopathy, nephropathy, and amputations).

The hyperglycemia and hyperinsulinemia observed in mice fed control high fat diets correlated with increased abdominal white adipose tissue deposition (Table 9). However, no differences in brown adipose tissue weights were observed between groups. The decreased abdominal adiposity observed in mice fed high fat diets supplemented with punicic acid when compared with mice fed the control diet could be caused by either suppressed adipogenesis or increased fatty acid consumption. Because fatty liver or enlarged viscera were not observed in mice fed punicic acid-supplemented diets, the decreased abdominal obesity is unlikely to be caused by decreased adipogenesis and it may be due to increased fatty acid consumption. All of which suggest that punicic acid could be utilized in the treatment and prevention of insulin resistance, abdominal obesity and Metabolic Syndrome.

It is understood that the invention is not confined to the particular construction and arrangement of parts herein illustrated and described, but embraces such modified forms thereof as come within the scope of the following claims.

BIBLIOGRAPHY

Bassaganya-Riera, J., R. Hontecillas, et al. (2001). "Effects of dietary conjugated linoleic acid in nursery pigs of dirty and clean environments on growth, empty body composition, and immune competence." *J Anim Sci* 79(3): 714-21.

Bassaganya-Riera, J., R. Hontecillas, et al. (2001). "Dietary conjugated linoleic acid modulates phenotype and effector functions of porcine cd8(+) lymphocytes." *J Nutr* 131(9): 2370-7.

Bassaganya-Riera, J., R. Hontecillas, et al. (2002). "Long-term influence of lipid nutrition on the induction of CD8(+) responses to viral or bacterial antigens." *Vaccine* 20(9-10): 1435-44.

Bassaganya-Riera, J., R. M. Pogranichniy, et al. (2003). "Conjugated Linoleic Acid Ameliorates Viral Infectivity in a Pig Model of Virally Induced Immunosuppression." *J Nutr* 133: 3204-3214.

Bassaganya-Riera, J., K. Reynolds, et al. (2004). "Activation of PPAR gamma and delta by conjugated linoleic acid mediates protection from experimental inflammatory bowel disease." *Gastroenterology* 127(3): 777-91.

Camilleri, M. (2003). "GI clinical research 2002-2003: The year in review." *Clinical Gastroenterology and Hepatology* 1: 415-420.

Hora, J. J., E. R. Maydew, et al. (2003). "Chemopreventive effects of pomegranate seed oil on skin tumor development in CD1 mice." *J Med Food* 6(3): 157-61.

Hornung, E., C. Pernstich, et al. (2002). "Formation of conjugated Delta11Delta13-double bonds by Delta12-linoleic acid (1,4)-acyl-lipid-desaturase in pomegranate seeds." *Eur J Biochem* 269(19): 4852-9.

Iwabuchi, M., J. Kohno-Murase, et al. (2003). "Delta 12-oleate desaturase-related enzymes associated with formation of conjugated trans-delta 11, cis-delta 13 double bonds." *J Biol Chem* 278(7): 4603-10.

Kim, N. D., R. Mehta, et al. (2002). "Chemopreventive and adjuvant therapetuic potential of pomegranate (Punica granatum) for human breast cancer." *Breast Cancer Research and Treatment* 71: 203-207.

Lichtenstein, G. R., M. Abreu, et al. (2003). Recent advances in the treatment of Crohn's colitis, The center for health care education, LLC.

Moller, D. E. and J. P. Berger (2003). "Role of PPARs in the regulation of obesity-related insulin sensitivity and inflammation." *Int J Obes Relat Metab Disord* 27 Suppl 3: S 17-21.

Rubins, H. B. and S. J. Robins (2000). "Conclusions from the VA-HIT study." *Am J Cardiol* 86(5): 543-4.

SAS (1988). SAS/STAT User's guide (Release 6.0.3). Cary, N.C., SAS Inst. Inc.

Saubermann, L. J., P. Beck, et al. (2000). "Activation of natural killer T cells by alpha-galactosylceramide in the presence of CD1d provides protection against colitis in mice." *Gastroenterology* 119(1): 119-28.

Strober, W., I. J. Fuss, et al. (2002). "The immunology of mucosal models of inflammation." *Annu Rev Immunol* 20: 495-549.

Vohl, M. C., R. Sladek, et al. (2004). "A survey of genes differentially expressed in subcutaneous and visceral adipose tissue in men." *Obes Res* 12(8): 1217-22.

What is claimed is:

1. A method of enhancing immune response comprising administering punicic acid to an animal in an amount effective to enhance immune response in the animal, wherein the animal is an animal undergoing a vaccination against a foreign antigen, and wherein the amount is between about 1 mg and 20 g per day.

2. The method of claim 1 wherein the animal undergoing the vaccination against the foreign antigen is administered an inactivated antigen.

3. The method of claim 1 wherein the administering the punicic acid to the animal undergoing the vaccination against the foreign antigen comprises administering the punicic acid prior to administering the foreign antigen.

4. The method of claim 1 wherein the administering enhances immune system development in the animal.

5. The method of claim 1 wherein the administering enhances development of an immune system component selected from the group consisting of a lymphoid organ and an immune cell.

6. The method of claim 1 wherein the administering enhances development of a lymphoid organ selected from the group consisting of thymus, spleen, lymph node, bronchi-associated lymphoid tissue, and gut-associated lymphoid tissue.

7. The method of claim 1 wherein the administering increases lymphocyte levels in the animal.

8. The method of claim 1 wherein the administering increases T cell levels in the animal.

9. The method of claim 1 wherein the administering increases levels of T cells selected from the group consisting of $CD4^+$ T cells, $CD8^+$ T cells, $CD3^+$ T cells, and T-cell receptor $\alpha\beta^+$ T cells in the animal.

10. The method of claim 1 wherein the administering increases proliferation of lymphocytes in response to a mitogenic stimulus.

11. The method of claim 1 wherein the punicic acid is administered in free fatty acid form.

12. The method of claim 1 wherein the punicic acid is administered in glyceride form.

13. The method of claim 1 wherein the punicic acid is administered with a pharmaceutically acceptable carrier.

14. The method of claim 13 wherein the pharmaceutically acceptable carrier is suitable for a route of administration selected from the group consisting of parenteral administration, oral administration, and rectal administration.

15. The method of claim 1 wherein the punicic acid is administered in a pharmaceutical composition, a nutritional product, a food supplement, a foodstuff, or a food composition.

16. The method of claim 15 wherein the pharmaceutical composition is administered in the form of a tablet, a capsule, a cachet, a lozenge, a solution, or an emulsion.

17. A method of enhancing immune response comprising administering in need of enhanced immune response in an amount effective to enhance immune response in the animal, wherein the animal is an animal undergoing a vaccination against a foreign antigen, and wherein the amount ranges from 10 mg/kg/day to 10,000 mg/kg/day.

18. The method of claim 1 wherein the animal in need of enhanced immune response is an animal undergoing a vaccination against a viral antigen.

19. The method of claim 17 wherein the animal in need of enhanced immune response is an animal undergoing a vaccination against a viral antigen.

* * * * *

UNITED STATES PATENT AND TRADEMARK OFFICE
CERTIFICATE OF CORRECTION

PATENT NO. : 8,822,543 B2
APPLICATION NO. : 13/370378
DATED : September 2, 2014
INVENTOR(S) : Josep Bassaganya-Riera It is certified that error appears in the above-identified patent and that said Letters Patent is hereby corrected as shown below:

Claims:

In claim 17 at column 26, line 65, delete "in need of enhanced immune response" and insert --punicic acid to an animal-- therefor.

Signed and Sealed this
Twenty-sixth Day of July, 2016

Michelle K. Lee
*Director of the United States Patent and Trademark Office*